(12) United States Patent
Blaeser et al.

(10) Patent No.: US 7,691,128 B2
(45) Date of Patent: Apr. 6, 2010

(54) PFO CLOSURE DEVICES AND RELATED METHODS OF USE

(75) Inventors: David J. Blaeser, Champlin, MN (US); Peter T. Keith, St. Paul, MN (US); Jerome K. Grudem, Jr., St. Louis Park, MN (US); Scott A. Olson, Zimmerman, MN (US); Steven S. Hackett, Maple Grove, MN (US); Thomas V. Ressemann, St. Cloud, MN (US); Joel D. Phillips, Minneapolis, MN (US); Mark R. Christianson, Darwin, MN (US); Dennis W. Wahr, Ann Arbor, MI (US)

(73) Assignee: St. Jude Medical, Cardiology Division, Inc., Minnetonka, MN (US)

( * ) Notice: Subject to any disclaimer, the term of this patent is extended or adjusted under 35 U.S.C. 154(b) by 106 days.

(21) Appl. No.: 11/249,317

(22) Filed: Oct. 14, 2005

(65) Prior Publication Data

US 2006/0036284 A1 Feb. 16, 2006

Related U.S. Application Data

(63) Continuation of application No. 10/138,565, filed on May 6, 2002.

(51) Int. Cl.
*A61B 17/08* (2006.01)
*A61D 1/00* (2006.01)
(52) U.S. Cl. .................. 606/216; 606/213; 623/1.11
(58) Field of Classification Search ................. 128/898; 606/213, 214, 215, 216; 623/1.11
See application file for complete search history.

(56) References Cited

U.S. PATENT DOCUMENTS 3,221,746 A 12/1965 Noble (Continued)

FOREIGN PATENT DOCUMENTS

AU 79531 3/1975

(Continued)

OTHER PUBLICATIONS

U.U. Babic, MD, "Experience with ASDOS for Transcatheter Closure of Atrial Septal Defect and Patent Foramen Ovale," *Current Interventional Cardiology Reports*, 2:177-183 (2000).

(Continued)

*Primary Examiner*—Todd E Manahan
*Assistant Examiner*—Michael G Mendoza
(74) *Attorney, Agent, or Firm*—Lerner, David, Littenberg, Krumholz & Mentlik, LLP

(57) ABSTRACT

Devices and methods for sealing a passageway formed by a patent foramen ovale (PFO track) in the heart are provided. One method includes providing an abrading device to the PFO track and abrading the tissue within the PFO track. The abraded tissue forming the PFO track is then held together under pressure, either via lowering right atrial pressure or via applying suction to the septum primum to pull it into apposition against the septum secundum. After a sufficient period of time, the pressure is released and the abraded tissue heals to form a robust seal over the PFO track. Additionally, several devices are provided which can be placed into the PFO track to apply adhesive to the walls of the PFO track. The devices may or may not be left within the PFO track. If the devices are not left within the PFO track, the walls of the PFO track, covered with adhesive, are brought into apposition with one another and adhered together. If the device is left within the PFO track, the device is flattened from an expanded configuration to a flattened configuration, and the walls of the PFO track, adhering to the outer surface of the device, are pulled toward each other as the device flattens. The device may also include interior structure to hold the device in a flattened configuration.

5 Claims, 12 Drawing Sheets

U.S. PATENT DOCUMENTS

| | | |
|---|---|---|
| 3,402,710 A | 9/1968 | Paleschuck |
| 3,540,431 A | 11/1970 | Uddin |
| 3,620,212 A | 11/1971 | Fannon |
| 3,638,388 A | 2/1972 | Kelly |
| 3,638,652 A | 2/1972 | Kelley |
| 3,657,744 A | 4/1972 | Ersek |
| 3,844,302 A | 10/1974 | Klein |
| 3,874,388 A | 4/1975 | King et al. |
| 4,007,743 A | 2/1977 | Blake et al. |
| 4,041,931 A | 8/1977 | Elliott et al. |
| 4,083,162 A | 4/1978 | Regan et al. |
| 4,214,587 A | 7/1980 | Sakura, Jr. |
| 4,309,776 A | 1/1982 | Berguer |
| 4,341,218 A | 7/1982 | Ue |
| 4,368,736 A | 1/1983 | Kaster |
| 4,485,816 A | 12/1984 | Krumme |
| 4,503,569 A | 3/1985 | Dotter |
| 4,592,754 A | 6/1986 | Gupte et al. |
| 4,603,693 A | 8/1986 | Contra et al. |
| 4,617,932 A | 10/1986 | Kornberg |
| 4,619,246 A | 10/1986 | Molgaard-Nielsen et al. |
| 4,629,451 A | 12/1986 | Winters et al. |
| 4,649,922 A | 3/1987 | Wiktor |
| 4,665,906 A | 5/1987 | Jervis |
| 4,681,588 A | 7/1987 | Ketharanathan |
| 4,710,192 A | 12/1987 | Liotta et al. |
| 4,733,665 A | 3/1988 | Palmaz |
| 4,739,762 A | 4/1988 | Palmaz |
| 4,748,982 A | 6/1988 | Horzewski et al. |
| 4,776,337 A | 10/1988 | Palmaz |
| 4,787,899 A | 11/1988 | Lazarus |
| 4,826,487 A | 5/1989 | Winter |
| 4,832,055 A | 5/1989 | Palestrant |
| 4,836,204 A | 6/1989 | Landymore et al. |
| 4,917,089 A | 4/1990 | Sideris |
| 4,921,484 A | 5/1990 | Hillstead |
| 4,994,069 A | 2/1991 | Ritchart |
| 5,041,082 A | 8/1991 | Shiber |
| 5,041,090 A | 8/1991 | Scheglov et al. |
| 5,042,707 A | 8/1991 | Taheri |
| 5,052,386 A | 10/1991 | Fischer, Jr. |
| 5,064,435 A | 11/1991 | Porter |
| 5,067,489 A | 11/1991 | Lind |
| 5,067,957 A | 11/1991 | Jervis |
| 5,078,736 A | 1/1992 | Behl |
| 5,098,440 A | 3/1992 | Hillstead |
| 5,104,399 A | 4/1992 | Lazarus |
| 5,108,420 A | 4/1992 | Marks |
| 5,122,136 A | 6/1992 | Guglielmi et al. |
| 5,122,156 A | 6/1992 | Granger et al. |
| 5,135,467 A | 8/1992 | Citron |
| 5,147,370 A | 9/1992 | McNamara et al. |
| 5,171,233 A | 12/1992 | Amplatz et al. |
| 5,171,259 A | 12/1992 | Inoue |
| 5,176,692 A | 1/1993 | Wilk et al. |
| 5,190,536 A | 3/1993 | Wood et al. |
| 5,192,301 A | 3/1993 | Kamiya et al. |
| 5,207,695 A | 5/1993 | Trout, III |
| 5,211,658 A | 5/1993 | Clouse |
| 5,211,683 A | 5/1993 | Maginot |
| 5,234,447 A | 8/1993 | Kaster et al. |
| 5,234,458 A | 8/1993 | Metals |
| 5,246,445 A | 9/1993 | Yachia et al. |
| 5,254,133 A | 10/1993 | Seid |
| 5,258,000 A | 11/1993 | Gianturco |
| 5,258,042 A | 11/1993 | Mehta |
| 5,275,622 A | 1/1994 | Lazarus et al. |
| 5,284,486 A | 2/1994 | Kotula et al. |
| 5,284,488 A | 2/1994 | Sideris |
| 5,304,184 A | 4/1994 | Hathaway et al. |
| 5,304,220 A | 4/1994 | Maginot |
| 5,306,234 A | 4/1994 | Johnson |
| 5,316,023 A | 5/1994 | Palmaz et al. |
| 5,334,217 A | 8/1994 | Das |
| 5,350,398 A | 9/1994 | Pavcnik et al. |
| 5,350,399 A | 9/1994 | Eriebacher et al. |
| 5,354,309 A | 10/1994 | Schnepp-Pesch et al. |
| 5,354,336 A | 10/1994 | Kelman et al. |
| 5,360,443 A | 11/1994 | Barone et al. |
| 5,366,462 A | 11/1994 | Kaster et al. |
| 5,375,612 A | 12/1994 | Cottenceau et al. |
| 5,385,562 A | 1/1995 | Adams et al. |
| 5,387,235 A | 2/1995 | Chuter |
| 5,391,156 A | 2/1995 | Hildwein et al. |
| 5,397,345 A | 3/1995 | Lazarus |
| 5,397,355 A | 3/1995 | Marin et al. |
| 5,417,699 A | 5/1995 | Klein et al. |
| 5,425,744 A | 6/1995 | Fagan et al. |
| 5,425,757 A | 6/1995 | Tiefenbrun et al. |
| 5,433,727 A | 7/1995 | Sideris |
| 5,443,454 A | 8/1995 | Tanabe et al. |
| 5,443,478 A | 8/1995 | Purdy |
| 5,443,497 A | 8/1995 | Venbrux |
| 5,451,235 A | 9/1995 | Lock et al. |
| 5,452,733 A | 9/1995 | Sterman et al. |
| 5,456,693 A | 10/1995 | Conston et al. |
| 5,456,712 A | 10/1995 | Maginot |
| 5,464,408 A | 11/1995 | Duc |
| 5,466,242 A | 11/1995 | Mori |
| 5,478,354 A | 12/1995 | Tovey et al. |
| 5,486,193 A | 1/1996 | Bourne et al. |
| 5,489,295 A | 2/1996 | Piplani et al. |
| 5,490,856 A | 2/1996 | Person et al. |
| 5,496,365 A | 3/1996 | Sgro |
| 5,507,769 A | 4/1996 | Marin et al. |
| 5,522,790 A | 6/1996 | Moll et al. |
| 5,522,822 A | 6/1996 | Phelps et al. |
| 5,522,836 A | 6/1996 | Palermo |
| 5,522,880 A | 6/1996 | Barone et al. |
| 5,522,882 A | 6/1996 | Gaterud et al. |
| 5,527,292 A | 6/1996 | Adams et al. |
| 5,527,322 A | 6/1996 | Klein et al. |
| 5,527,338 A | 6/1996 | Purdy |
| 5,545,214 A | 8/1996 | Stevens |
| 5,562,728 A | 10/1996 | Lazarus et al. |
| 5,597,378 A | 1/1997 | Jervis |
| 5,607,444 A | 3/1997 | Lam |
| 5,614,204 A | 3/1997 | Cochrum |
| 5,617,878 A | 4/1997 | Taheri |
| 5,618,311 A | 4/1997 | Gryskiewicz |
| 5,634,292 A | 6/1997 | Hart |
| 5,634,936 A | 6/1997 | Linden et al. |
| 5,645,558 A | 7/1997 | Horton |
| 5,653,747 A | 8/1997 | Dereume |
| 5,669,933 A | 9/1997 | Simon et al. |
| 5,676,670 A | 10/1997 | Kim |
| 5,681,336 A | 10/1997 | Clement et al. |
| 5,693,067 A | 12/1997 | Purdy |
| 5,693,083 A | 12/1997 | Baker et al. |
| 5,695,504 A | 12/1997 | Gifford et al. |
| 5,702,412 A | 12/1997 | Popov et al. |
| 5,702,421 A | 12/1997 | Schneidt |
| 5,709,224 A | 1/1998 | Behl et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,735,290 A | 4/1998 | Sterman et al. |
| 5,741,297 A | 4/1998 | Simon |
| 5,749,894 A | 5/1998 | Engelson |
| 5,766,219 A | 6/1998 | Horton |
| 5,775,778 A | 7/1998 | Riley |
| 5,776,097 A | 7/1998 | Massoud |
| 5,776,162 A | 7/1998 | Kleshinski |

| Patent No. | Date | Inventor |
|---|---|---|
| 5,782,860 A | 7/1998 | Epstein et al. |
| 5,797,960 A | 8/1998 | Stevens et al. |
| 5,830,228 A | 11/1998 | Knapp et al. |
| 5,833,698 A | 11/1998 | Hinchliffe et al. |
| 5,836,968 A | 11/1998 | Simon et al. |
| 5,840,064 A | 11/1998 | Liprie |
| 5,843,118 A | 12/1998 | Sepetka et al. |
| 5,843,164 A | 12/1998 | Frantzen et al. |
| 5,843,170 A | 12/1998 | Ahn |
| 5,843,175 A | 12/1998 | Frantzen |
| 5,846,261 A | 12/1998 | Kotula et al. |
| 5,849,005 A | 12/1998 | Garrison et al. |
| 5,853,419 A | 12/1998 | Imran |
| 5,853,422 A | 12/1998 | Huebsch et al. |
| 5,861,003 A | 1/1999 | Latson et al. |
| 5,865,791 A | 2/1999 | Whayne et al. |
| 5,868,762 A | 2/1999 | Cragg et al. |
| 5,879,366 A | 3/1999 | Shaw et al. |
| 5,885,258 A | 3/1999 | Sachdeva |
| 5,891,558 A | 4/1999 | Bell et al. |
| 5,904,680 A | 5/1999 | Kordis et al. |
| 5,904,703 A | 5/1999 | Gilson |
| 5,906,207 A | 5/1999 | Shen |
| 5,910,155 A | 6/1999 | Ratcliff et al. |
| 5,919,200 A | 7/1999 | Stambaugh et al. |
| 5,921,995 A | 7/1999 | Kleshinski |
| 5,922,022 A | 7/1999 | Nash et al. |
| 5,935,148 A | 8/1999 | Villar et al. |
| 5,944,738 A | 8/1999 | Amplatz et al. |
| 5,976,159 A | 11/1999 | Bolduc et al. |
| 5,976,178 A | 11/1999 | Goldsteen et al. |
| 6,013,190 A | 1/2000 | Berg et al. |
| 6,021,340 A | 2/2000 | Randolph et al. |
| 6,024,756 A | 2/2000 | Huebsch et al. |
| 6,026,814 A | 2/2000 | LaFontaine et al. |
| 6,035,856 A | 3/2000 | LaFontaine et al. |
| 6,036,702 A | 3/2000 | Bachinski et al. |
| 6,036,716 A | 3/2000 | Kruchinin et al. |
| 6,074,416 A | 6/2000 | Berg et al. |
| 6,076,012 A | 6/2000 | Swanson et al. |
| 6,079,414 A | 6/2000 | Roth |
| 6,080,182 A | 6/2000 | Shaw et al. |
| 6,113,612 A | 9/2000 | Swanson et al. |
| 6,120,432 A | 9/2000 | Sullivan et al. |
| 6,123,715 A | 9/2000 | Amplatz |
| 6,124,523 A | 9/2000 | Banas et al. |
| 6,132,438 A | 10/2000 | Fleischman et al. |
| 6,152,144 A | 11/2000 | Lesh et al. |
| 6,165,196 A | 12/2000 | Stack et al. |
| 6,168,622 B1 | 1/2001 | Mazzocchi |
| 6,171,329 B1 | 1/2001 | Shaw et al. |
| 6,174,322 B1 | 1/2001 | Schneidt |
| 6,193,734 B1 | 2/2001 | Bolduc et al. |
| 6,206,907 B1 | 3/2001 | Marino et al. |
| 6,210,338 B1 | 4/2001 | Afremov et al. |
| 6,214,029 B1 | 4/2001 | Thill et al. |
| 6,231,561 B1 | 5/2001 | Frazier et al. |
| 6,241,678 B1 | 6/2001 | Afremov et al. |
| 6,290,674 B1 | 9/2001 | Roue et al. |
| 6,325,815 B1 | 12/2001 | Kuslieka et al. |
| 6,334,864 B1 | 1/2002 | Amplatz et al. |
| 6,368,338 B1 | 4/2002 | Konya et al. |
| 6,368,339 B1 | 4/2002 | Amplatz |
| 6,371,971 B1 | 4/2002 | Tsugita et al. |
| 6,379,368 B1 | 4/2002 | Corcoran et al. |
| 6,391,044 B1 | 5/2002 | Yadav et al. |
| 6,401,720 B1 | 6/2002 | Stevens et al. |
| 6,402,746 B1 | 6/2002 | Whayne et al. |
| 6,402,772 B1 | 6/2002 | Amplatz |
| 6,419,669 B1 | 7/2002 | Frazier et al. |
| 6,432,123 B2 | 8/2002 | Schwartz et al. |
| 6,436,088 B2 * | 8/2002 | Frazier et al. ............... 604/508 |
| 6,440,152 B1 | 8/2002 | Gainor et al. |
| 6,447,531 B1 | 9/2002 | Amplatz |
| 6,458,100 B2 | 10/2002 | Roue et al. |
| 6,468,291 B2 | 10/2002 | Bates et al. |
| 6,468,301 B1 | 10/2002 | Amplatz et al. |
| D466,936 S | 12/2002 | Shaw et al. |
| 6,491,707 B2 | 12/2002 | Makower et al. |
| 6,506,204 B2 | 1/2003 | Mazzocchi |
| 6,508,828 B1 | 1/2003 | Akerfeldt |
| 6,511,496 B1 | 1/2003 | Huter et al. |
| 6,527,746 B1 | 3/2003 | Oslund et al. |
| 6,537,299 B1 | 3/2003 | Hogendijk et al. |
| 6,540,712 B1 | 4/2003 | Parodi et al. |
| 6,551,303 B1 | 4/2003 | VanTassel et al. |
| 6,551,344 B2 | 4/2003 | Thill |
| 6,562,058 B2 | 5/2003 | Seguin et al. |
| 6,599,308 B2 | 7/2003 | Amplatz |
| 6,599,311 B1 | 7/2003 | Biggs et al. |
| 6,623,508 B2 | 9/2003 | Shaw et al. |
| 6,641,557 B1 | 11/2003 | Frazier et al. |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,660,015 B1 | 12/2003 | Berg |
| 6,682,546 B2 | 1/2004 | Amplatz |
| 6,689,150 B1 | 2/2004 | VanTassel et al. |
| 6,702,835 B2 | 3/2004 | Ginn |
| 6,712,804 B2 | 3/2004 | Roue et al. |
| 6,712,836 B1 | 3/2004 | Berg |
| 6,776,754 B1 | 8/2004 | Wilk |
| 6,776,784 B2 | 8/2004 | Ginn |
| 6,911,037 B2 | 6/2005 | Gainor et al. |
| 6,913,614 B2 | 7/2005 | Marino et al. |
| 7,220,265 B2 * | 5/2007 | Chanduszko et al. ........ 606/139 |
| 2001/0000797 A1 | 5/2001 | Mazzocchi |
| 2001/0014800 A1 | 8/2001 | Frazier et al. |
| 2001/0021872 A1 | 9/2001 | Bailey et al. |
| 2001/0034537 A1 | 10/2001 | Shaw et al. |
| 2001/0037129 A1 | 11/2001 | Thill |
| 2001/0041914 A1 | 11/2001 | Frazier et al. |
| 2001/0049492 A1 | 12/2001 | Frazier et al. |
| 2002/0022860 A1 | 2/2002 | Borillo et al. |
| 2002/0026094 A1 | 2/2002 | Roth |
| 2002/0029061 A1 | 3/2002 | Amplatz et al. |
| 2002/0035374 A1 | 3/2002 | Borillo et al. |
| 2002/0042625 A1 | 4/2002 | Stack et al. |
| 2002/0068950 A1 | 6/2002 | Corcoran et al. |
| 2002/0111647 A1 | 8/2002 | Khairkhahan et al. |
| 2002/0123759 A1 | 9/2002 | Amplatz |
| 2002/0123760 A1 | 9/2002 | Amplatz |
| 2002/0138094 A1 | 9/2002 | Borillo et al. |
| 2002/0138095 A1 | 9/2002 | Mazzocchi et al. |
| 2002/0161395 A1 | 10/2002 | Douk et al. |
| 2002/0169474 A1 | 11/2002 | Kusleika et al. |
| 2002/0169475 A1 | 11/2002 | Gainor et al. |
| 2002/0183787 A1 | 12/2002 | Wahr et al. |
| 2002/0198561 A1 | 12/2002 | Amplatz |
| 2002/0198563 A1 | 12/2002 | Gainor et al. |
| 2003/0023262 A1 | 1/2003 | Welch |
| 2003/0023266 A1 | 1/2003 | Borillo et al. |
| 2003/0028213 A1 | 2/2003 | Thill et al. |
| 2003/0045901 A1 | 3/2003 | Opolski |
| 2003/0057156 A1 | 3/2003 | Peterson et al. |
| 2003/0120337 A1 | 6/2003 | Van Tassel et al. |
| 2003/0139819 A1 | 7/2003 | Beer et al. |
| 2003/0144694 A1 | 7/2003 | Chanduszko et al. |
| 2003/0181942 A1 | 9/2003 | Sutton et al. |
| 2003/0191495 A1 | 10/2003 | Ryan et al. |
| 2003/0195530 A1 | 10/2003 | Thill |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0212432 A1 | 11/2003 | Khairkhahan et al. |
| 2003/0225421 A1 | 12/2003 | Peavey et al. |

| | | | |
|---|---|---|---|
| 2004/0073242 A1 | 4/2004 | Chanduszko | |
| 2004/0092973 A1 | 5/2004 | Chanduszko | |
| 2004/0098047 A1 | 5/2004 | Frazier et al. | |
| 2004/0098121 A1 | 5/2004 | Opolski | |
| 2004/0133236 A1 | 7/2004 | Chanduszko | |
| 2004/0143277 A1 | 7/2004 | Marino et al. | |
| 2004/0143291 A1 | 7/2004 | Corcoran et al. | |
| 2004/0143293 A1 | 7/2004 | Marino et al. | |
| 2004/0143294 A1 | 7/2004 | Corcoran et al. | |
| 2004/0176799 A1 | 9/2004 | Chanduszko et al. | |
| 2004/0186486 A1 | 9/2004 | Roue et al. | |
| 2004/0193147 A1 | 9/2004 | Malecki | |
| 2004/0215230 A1 | 10/2004 | Frazier et al. | |
| 2004/0225324 A1 | 11/2004 | Marino et al. | |
| 2004/0230185 A1 | 11/2004 | Malecki et al. | |
| 2004/0267191 A1 | 12/2004 | Gifford, III et al. | |
| 2005/0021016 A1 | 1/2005 | Malecki et al. | |
| 2005/0033327 A1 | 2/2005 | Galnor et al. | |
| 2005/0034735 A1 | 2/2005 | Deem et al. | |
| 2005/0038470 A1 | 2/2005 | van der Burg et al. | |
| 2005/0043711 A1 | 2/2005 | Corcoran et al. | |
| 2005/0043759 A1 | 2/2005 | Chanduszko | |
| 2005/0059983 A1 | 3/2005 | Opolski et al. | |
| 2005/0065546 A1 | 3/2005 | Corcoran et al. | |
| 2005/0065547 A1 | 3/2005 | Marino et al. | |
| 2005/0065548 A1 | 3/2005 | Marino et al. | |
| 2005/0080406 A1 | 4/2005 | Malecki et al. | |
| 2005/0090857 A1 | 4/2005 | Kusleika et al. | |
| 2005/0101984 A1 | 5/2005 | Chanduszko et al. | |
| 2005/0113861 A1 | 5/2005 | Corcoran et al. | |
| 2005/0113868 A1 | 5/2005 | Devellian et al. | |
| 2005/0119675 A1 | 6/2005 | Adams et al. | |
| 2005/0131401 A1 | 6/2005 | Malecki et al. | |
| 2005/0131460 A1 | 6/2005 | Gifford, III et al. | |
| 2005/0155612 A1 | 7/2005 | Matsuura et al. | |

FOREIGN PATENT DOCUMENTS

| | | | |
|---|---|---|---|
| AU | 670239 | | 1/1994 |
| CA | 2057018 | | 10/1991 |
| DE | 2822603 | A1 | 11/1979 |
| DE | 233303 | A1 | 2/1986 |
| DE | 195 42 733 | | 7/1997 |
| EP | 362113 | A1 | 4/1990 |
| EP | 0539237 | A1 | 4/1993 |
| EP | 541063 | A | 5/1993 |
| EP | 0637454 | A1 | 2/1995 |
| EP | 0680734 | A2 | 11/1995 |
| EP | 0684022 | A2 | 11/1995 |
| EP | 0701800 | A1 | 3/1996 |
| EP | 0712614 | A1 | 5/1996 |
| EP | 0732088 | A2 | 9/1996 |
| EP | 0732089 | A2 | 9/1996 |
| EP | 0807444 | A2 | 11/1997 |
| EP | 0 920 842 | A1 | 6/1999 |
| EP | 1175867 | A2 | 1/2002 |
| EP | 1281355 | A2 | 2/2003 |
| EP | 1013227 | B | 8/2006 |
| FR | 2641692 | | 1/1990 |
| GB | 489316 | | 7/1938 |
| GB | 2 269 321 | A | 2/1994 |
| GB | 2269104 | A | 2/1994 |
| JP | 2001-517472 | | 10/2001 |
| WO | WO 89/08433 | A1 | 9/1989 |
| WO | WO 91/05088 | | 4/1991 |
| WO | WO 93/00868 | A1 | 1/1993 |
| WO | WO 93/13712 | A | 7/1993 |
| WO | WO 93/20757 | A2 | 10/1993 |
| WO | WO 94/01056 | A1 | 1/1994 |
| WO | WO 95/21592 | A1 | 8/1995 |
| WO | WO 95/26695 | | 10/1995 |
| WO | WO 95/28885 | | 11/1995 |
| WO | WO 95/32757 | A1 | 12/1995 |
| WO | WO 96/01591 | A1 | 1/1996 |
| WO | WO 96/01599 | A1 | 1/1996 |
| WO | WO 96/14808 | A1 | 5/1996 |
| WO | WO 96/18361 | A1 | 6/1996 |
| WO | WO 96/22745 | A1 | 8/1996 |
| WO | WO 96/25886 | A | 8/1996 |
| WO | WO 96/25897 | A2 | 8/1996 |
| WO | WO 96/32882 | | 10/1996 |
| WO | WO 96/40356 | | 12/1996 |
| WO | WO 97/13463 | A1 | 4/1997 |
| WO | WO 97/13471 | A1 | 4/1997 |
| WO | WO 97/27898 | A1 | 8/1997 |
| WO | WO 97/41778 | A | 11/1997 |
| WO | WO/97 41779 | A1 | 11/1997 |
| WO | WO 97/42878 | | 11/1997 |
| WO | WO 98/01086 | | 1/1998 |
| WO | WO 98/02099 | A1 | 1/1998 |
| WO | WO 98/03118 | A1 | 1/1998 |
| WO | WO 98/08462 | A | 3/1998 |
| WO | WO 98/09671 | | 3/1998 |
| WO | WO 98/19629 | A2 | 5/1998 |
| WO | WO 98/19631 | A1 | 5/1998 |
| WO | WO 98/26732 | A1 | 6/1998 |
| WO | WO 98/27868 | | 7/1998 |
| WO | WO 98/27894 | | 7/1998 |
| WO | WO 98/19629 | A3 | 9/1998 |
| WO | WO 98/38939 | A1 | 9/1998 |
| WO | WO 98/38941 | A1 | 9/1998 |
| WO | WO 98/38942 | A1 | 9/1998 |
| WO | WO 98/42262 | | 10/1998 |
| WO | WO 98/55027 | A2 | 12/1998 |
| WO | WO 99/07289 | | 2/1999 |
| WO | WO 99/17816 | | 4/1999 |
| WO | WO 99/38454 | | 5/1999 |
| WO | WO 99/39646 | | 8/1999 |
| WO | WO 99/62408 | A1 | 12/1999 |
| WO | WO 00/10452 | | 3/2000 |
| WO | WO 00/12012 | | 3/2000 |
| WO | WO 00/16705 | | 3/2000 |
| WO | WO 00/27292 | | 5/2000 |
| WO | WO 00/56245 | | 9/2000 |
| WO | 01/21247 | | 3/2001 |
| WO | WO 01/15629 | A1 | 3/2001 |
| WO | WO 01/17435 | A1 | 3/2001 |
| WO | WO 01/30266 | A1 | 5/2001 |
| WO | WO 01/30267 | A1 | 5/2001 |
| WO | WO 01/30268 | A1 | 5/2001 |
| WO | WO 01/72367 | A1 | 10/2001 |
| WO | WO 01/87163 | A1 | 11/2001 |
| WO | WO 01/91844 | A1 | 12/2001 |
| WO | WO 02/15793 | A2 | 2/2002 |
| WO | WO 02/24106 | A2 | 3/2002 |
| WO | WO 02/098298 | | 12/2002 |
| WO | WO 03/009880 | A2 | 2/2003 |
| WO | WO 03/053493 | A3 | 7/2003 |
| WO | WO 03/059152 | A2 | 7/2003 |
| WO | WO 03/082076 | A2 | 10/2003 |
| WO | WO 03/103476 | A2 | 12/2003 |
| WO | WO 2005/006990 | A2 | 1/2005 |
| WO | WO 2005/027752 | A1 | 3/2005 |
| WO | WO 2005/039419 | A1 | 5/2005 |

OTHER PUBLICATIONS

Terry King et al., "Secundum Atrial Septal Defect," *JAMA*, 235/23:2506-2509 (1976).

Makram R. Ebeid, MD, "Percutaneous Catheter Closure of Secundum Atrial Septal Defects: A Review," *J. Invas. Cardiol.* 14:25-31 (2002).

Brochure and Instructions for Use for CardioSeal® Septal Occlusion System, "An Alternative FDA Approved Solution for Patients Needing Closure of Ventricular Septal Defects," NMT Medical Inc., pp. 1-24 (1999).

U.S. Appl. No. 10/138,565, filed May 6, 2002.

Office Action from Japanese Application No. 2004-502838, dated Apr. 9, 2009.

* cited by examiner

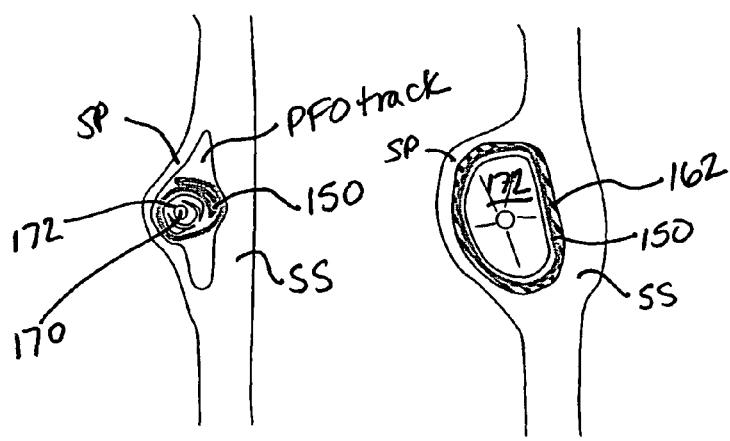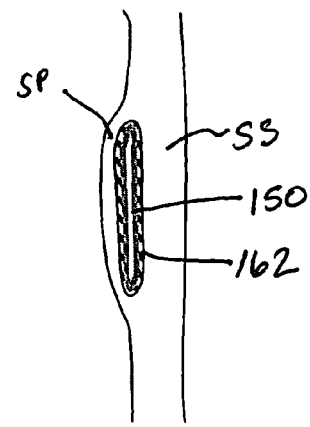
Fig. 23　　　Fig. 24　　　Fig. 25

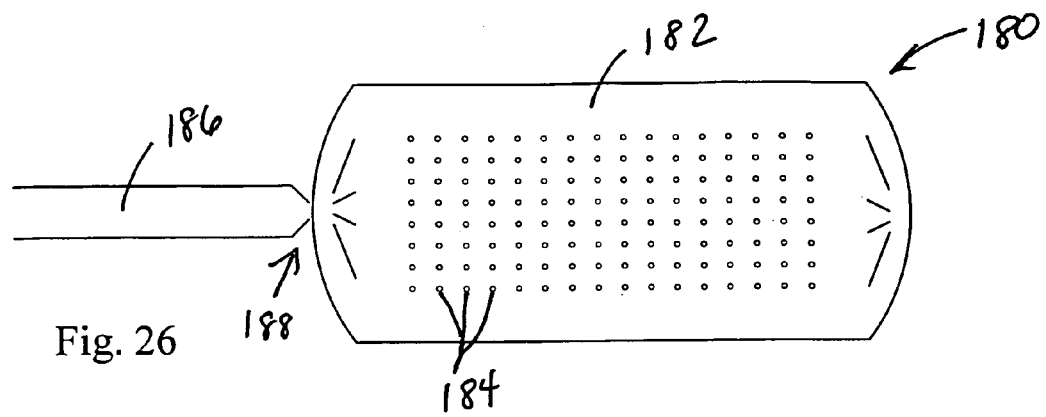
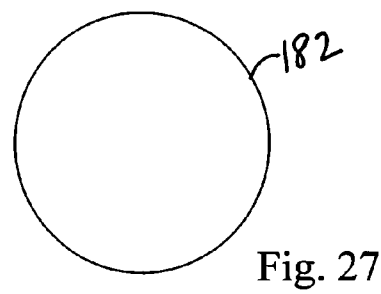
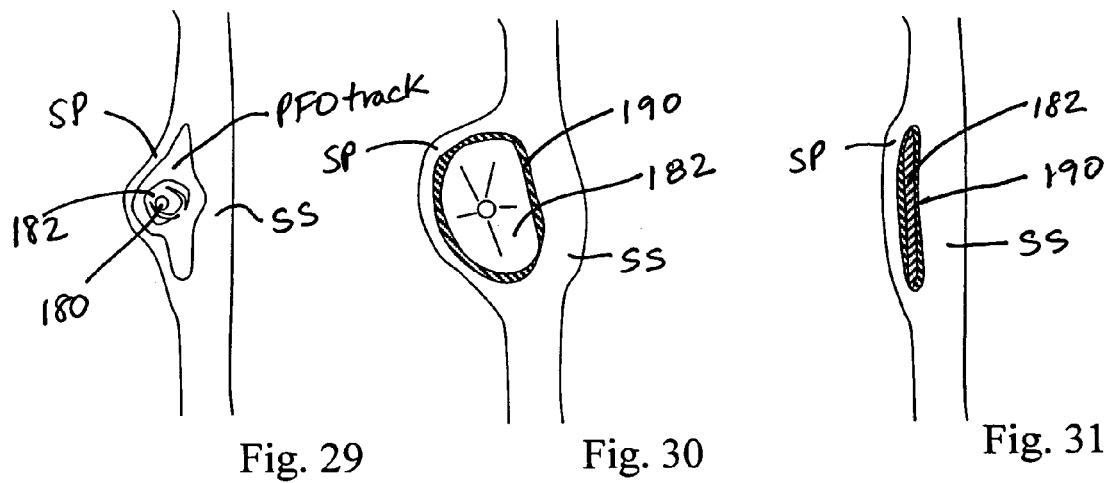
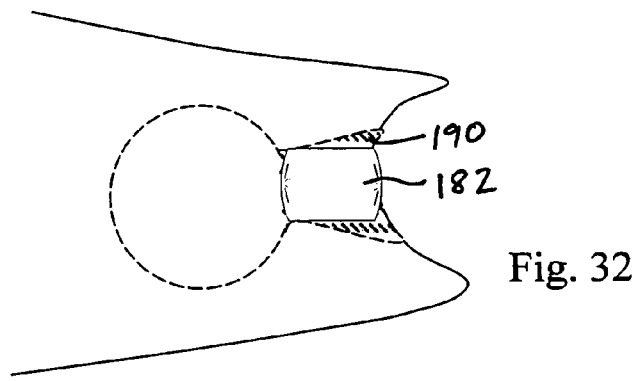

PFO CLOSURE DEVICES AND RELATED METHODS OF USE

This application is a continuation of U.S. application Ser. No. 10/138,565, filed May 6, 2002, entitled "PFO Closure Devices and Related Methods of Use," the entire disclosure of which is incorporated herein by reference.

FIELD OF THE INVENTION

This invention relates to devices for closing a passageway in a body, for example a patent foramen ovale in a heart, and related methods of using such closure devices for sealing the passageway.

BACKGROUND OF THE INVENTION

FIG. 1 shows a short-axis view of the heart at the level of the right atrium (RA) and left atrium (LA), in a plane generally parallel to the atrio-ventricular groove, and at the level of the aortic valve. This view is looking from caudal to cranial. FIG. 1 also shows the septum primum (SP), a flap-like structure, which normally covers the foramen ovale, an opening in the septum secundum (SS) of the heart. In utero, the foramen ovale serves as a physiologic conduit for right-to-left shunting of blood in the fetal heart. After birth, with the establishment of pulmonary circulation, the increased left atrial blood flow and pressure presses the septum primum (SP) against the walls of the septum secundum (SS), covering the foramen ovale and resulting in functional closure of the foramen ovale. This closure is usually followed by anatomical closure of the foramen ovale due to fusion of the septum primum (SP) to the septum secundum (SS).

Where anatomical closure of the foramen ovale does not occur, a patent foramen ovale (PFO) is created. A patent foramen ovale is a persistent, usually flap-like opening between the atrial septum primum (SP) and septum (SS) of a heart. A patent foramen ovale results when either partial or no fusion of the septum primum (SP) to the septum secundum (SS) occurs. In the case of partial fusion or no fusion, a persistent passageway (PFO track) exists between the septum primum (SP) and septum secundum (SS). This opening or passageway is typically parallel to the plane of the SP, and has a mouth which is generally oval in shape. FIG. 2 shows the opening of the PFO track viewed from an end of the track. Normally the opening is relatively tall, but quite narrow. The opening may be held closed due to the mean pressure in the LA being typically higher than in the RA. In this manner, the SP acts like a one-way valve, preventing fluid communication between the right and left atria through the PFO track. However, at times, the pressure may temporarily be higher in the RA, causing the PFO track to open up and allow some fluid to pass from the RA to the LA, as indicated in FIG. 3. Although the PFO track is often held closed, the endothelialized surfaces of the tissues forming the PFO track prevent the tissue from healing together and permanently closing the PFO track. As can be seen in FIG. 4, (a view from line "C-C" of FIG. 1), the SP is firmly attached to the SS around most of the perimeter of the Fossa Ovalis, but has an opening along one side. The SP is often connected, as shown, by two or more extensions of tissue along the sides of the PFO track.

Studies have shown that a relatively large percentage of adults have a patent foramen ovale (PFO). It is believed that embolism via a PFO may be a cause of a significant number of ischemic strokes, particularly in relatively young patients. It has been estimated that in 50% of cryptogenic strokes, a PFO is present. Blood clots which form in the venous circulation (e.g., the legs) can embolize, and may enter the arterial circulation via the PFO, subsequently entering the cerebral circulation, resulting in an embolic stroke. Blood clots may also form in the vicinity of the PFO, and embolize into the arterial circulation and into the cerebral circulation. Patients suffering a cryptogenic stroke or a transient ischemic attack (TIA) in the presence of a PFO often are considered for medical therapy to reduce the risk of a recurrent embolic event.

Pharmacological therapy often includes oral anticoagulants or antiplatelet agents. These therapies may lead to certain side effects, including hemorrhage. If pharmacologic therapy is unsuitable, open heart surgery may be employed to close a PFO with stitches, for example. Like other open surgical treatments, this surgery is highly invasive, risky, requires general anesthesia, and may result in lengthy recuperation.

Nonsurgical closure of PFOs is possible with umbrella-like devices developed for percutaneous closure of atrial septal defects (ASD) (a condition where there is not a well-developed septum primum (SP)). Many of these conventional devices used for ASDs, however, are technically complex, bulky, and difficult to deploy in a precise location. In addition, such devices may be difficult or impossible to retrieve and/or reposition should initial positioning not be satisfactory. Moreover, these devices are specially designed for ASDs and therefore may not be suitable to close and seal a PFO, particularly because the septum primum (SP) overlaps the septum secundum (SS).

SUMMARY OF THE INVENTION

In accordance with the invention, methods and devices for closing a passageway in a body, and more specifically closing a patent foramen ovale (PFO), are provided.

According to one aspect of the invention, a method of sealing a passageway in a heart is provided. The method includes advancing an abrasion device into the passageway to be sealed, abrading at least a portion of the tissue surfaces forming the passageway, withdrawing the abrasion device from the passageway, and forcing abraded portions of the tissue surfaces of the passageway against one another for a period of time.

According to another aspect of the invention, a device for sealing a passageway in a human body is provided. The device comprises a catheter having an distal portion, and at least one suture lumen, the at least one suture lumen containing a suture having an anchor at an end of the suture.

According to yet another aspect of the invention, an assembly for sealing a passageway in a human body is provided. The assembly includes a delivery catheter, a suture connected to a barbed anchor, and a support tube configured to surround and support the suture.

According to a further aspect of the invention, a method of sealing a passageway in a heart is provided. The method comprises advancing a hollow tubular structure into the passageway to be sealed, engaging the walls of the passageway with the hollow tubular structure, and flattening the hollow tubular structure.

According to another aspect of the invention, a method of sealing a passageway in a heart includes advancing a catheter into the passageway, applying adhesive to the walls of the passageway, withdrawing the catheter from the passageway, and forcing portions of the walls of the passageway against one another for a period of time sufficient to allow the adhesive to at least partially cure.

According to yet another aspect of the invention, a method of sealing a passageway in a heart is provided. The method comprises advancing a delivery device having an expandable end into the passageway, wherein the delivery device includes at least two suture lumens, each suture lumen having an open end positioned in the passageway when the delivery device is advanced into the passageway, expanding the expandable end, advancing a suture-anchor assembly out of the end of each suture lumen, penetrating the tissue forming the passageway with an anchor of each suture-anchor assembly, and pulling the passageway closed with the anchored sutures.

According to another aspect of the invention, a method of sealing a passageway between a septum primum and a septum secundum in a heart is provided. The method includes advancing a delivery catheter into the right atrium, advancing an anchor and suture assembly out of the deliver catheter, and passing the anchor and suture assembly through the septum secundum and through the septum primum.

Additional advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIGS. 23-25 are cross-sectional views of the self-flattening closure device of FIG. 15, with the delivery catheter of FIG. 22, being deployed within a PFO track, according to an aspect of the present invention.

FIG. 26 is a side view of a porous balloon catheter according to one aspect of the present invention.

FIG. 27 is a cross-sectional view of the porous balloon catheter of FIG. 26 in an inflated condition.

FIG. 28 is a cross-sectional view of the porous balloon catheter of FIG. 26 in a deflated condition.

FIGS. 29-31 are cross-sectional views of the porous balloon catheter of FIG. 26 being deployed within a PFO track, according to an aspect of the present invention.

FIG. 32 is a longitudinal cross-sectional view of a portion of the porous balloon catheter of FIG. 26 filling and sealing the PFO track after deployment, according to an aspect of the present invention.

DESCRIPTION OF THE EMBODIMENTS

Reference will now be made in detail to embodiments of the invention, examples of which are illustrated in the accompanying drawings. Wherever possible, the same reference numbers will be used throughout the drawings to refer to the same or like parts.

The various figures show embodiments of patent foramen ovale (PFO) closure devices and methods of using the devices to close a PFO. The devices and related methods are described herein in connection with use in sealing a PFO. These devices, however, also are suitable for closing other openings or passageways, including other such openings in the heart, for example atrial septal defects, ventricular septal defects, and patent ductus arterioses, and openings or passageways in other portions of a body such as an arteriovenous fistula. The invention therefore is not limited to use of the inventive closure devices to close PFOs.

Figure 1:
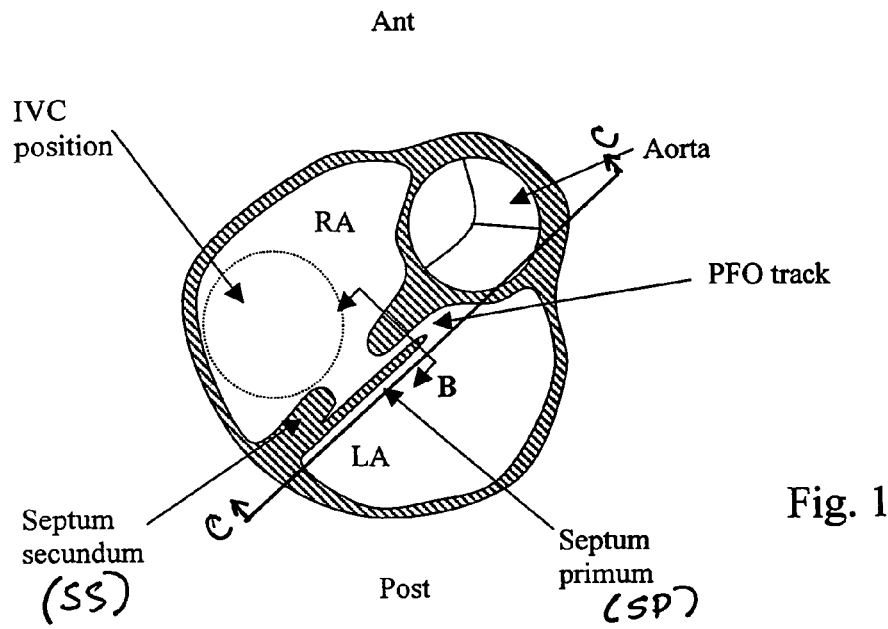
FIG. 1 is a short-axis view of the heart at the level of the right atrium (RA) and left atrium (LA), in a plane generally parallel to the atrio-ventricular groove, and at the level of the aortic valve, showing a PFO track.
Figure 2:
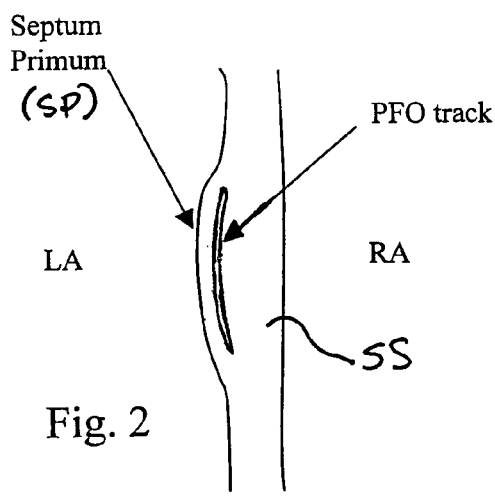
FIG. 2 is a cross-sectional view of the PFO track of FIG. 1 taken along line B-B, the PFO in a "closed" configuration.
Figure 3:
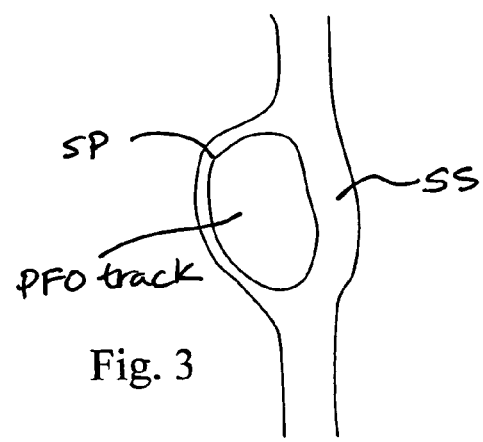
FIG. 3 is a cross-sectional view of the PFO track of FIG. 2 in an "open" configuration.
Figure 4:
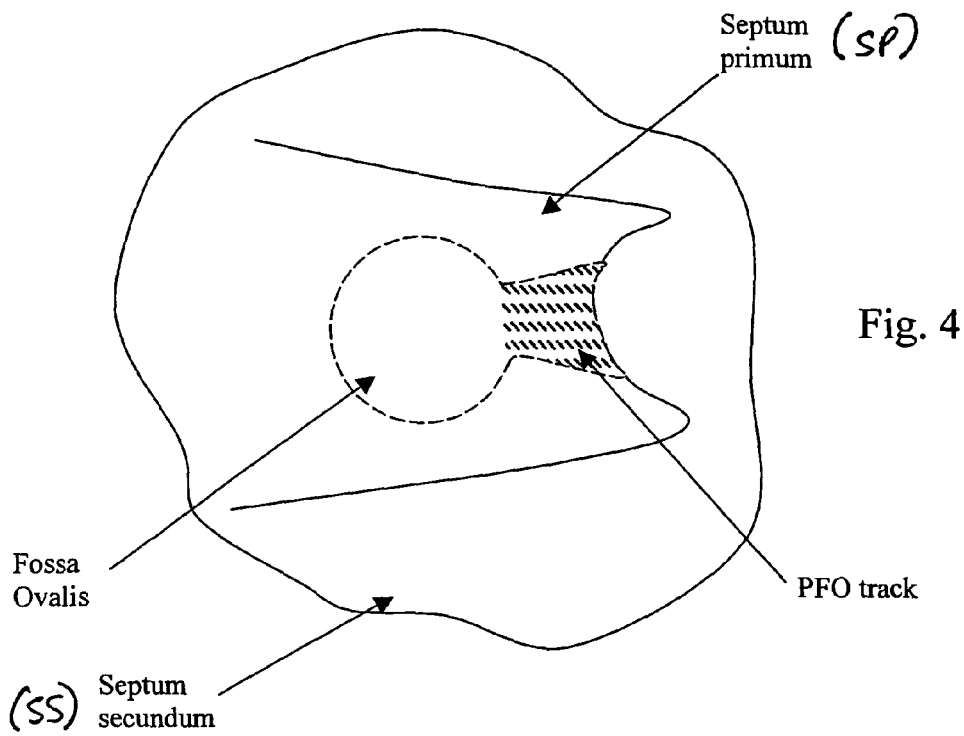
FIG. 4 is cross-sectional view of the PFO track of FIG. 1 taken along line C-C.
Figure 5:
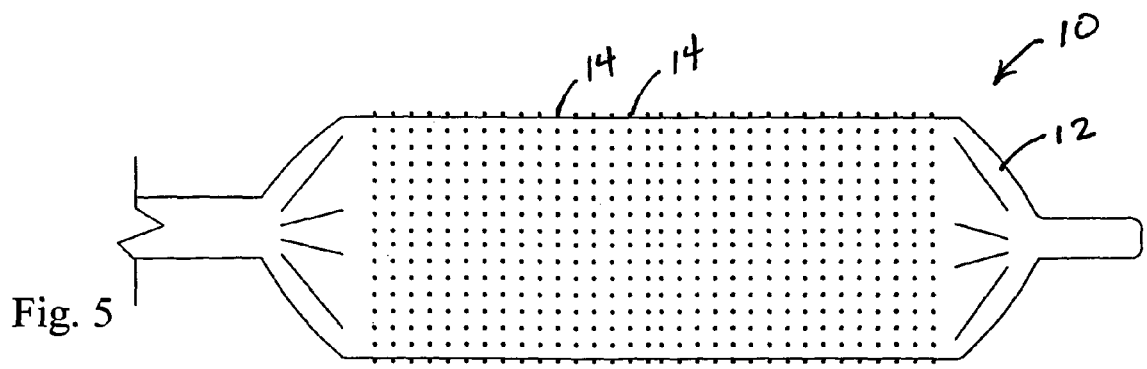
FIG. 5 is a perspective view of an abrasion device, according to an aspect of the present invention.

According to one aspect of the present invention, an abrasion device is provided. As embodied herein and shown in FIG. 5, an abrasion device 10 is provided for use in a method of closing a PFO track (referenced as PFO in the Figs.). The abrasion device 10 preferably includes an inflatable balloon 12 having a plurality of abrasive elements 14 attached to an outer surface of the balloon 12. The abrasive elements 14 protrude beyond the outer surface of the balloon 12 and may form a surface similar to that of sandpaper. The abrasive elements 14 may be formed by abrasive material, for example microbeads, attached to the outer surface of the balloon 12 with an adhesive. Alternatively, the abrasive elements may be formed by any other suitable means. The adhesive should be strong enough to ensure that the abrasive material cannot come loose during contact with structures within the body, and should be flexible enough such that it does not inhibit the ability of the balloon to be inflated and deflated. An example of a preferred adhesive is a flexible adhesive such as polyurethane or epoxy.

Alternatively, the abrasive elements may be formed by a plurality of small protuberances molded on the outside of the balloon, such that the outer surface of the balloon 12 has an abrasive quality once it is inflated. The abrasion device 10 need not utilize a balloon 12, but could be fabricated of an expandable material having an abrasive quality or a non-expandable tube-like element with an abrasive quality.

Figure 6:
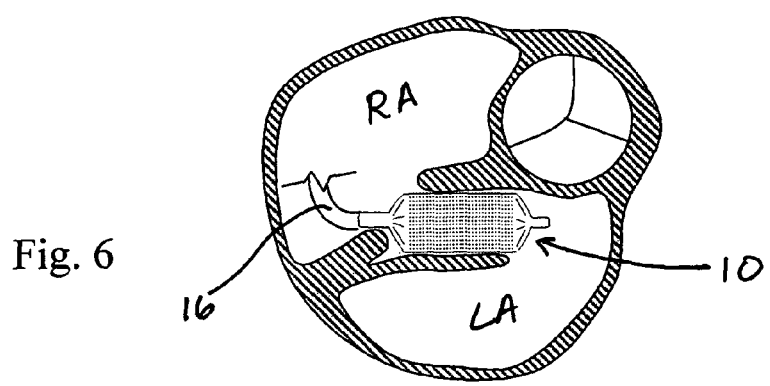
FIG. 6 is a perspective view of the abrasion device of FIG. 5 positioned within a PFO track, according to an aspect of the present invention.

The abrasion device 10 is attached to a catheter 16 (FIG. 6), which contains a lumen (not shown) for inflating and deflating the balloon 12. The abrasion device 10 is passed from an access site, preferably in the femoral vein, into the PFO track. The abrasion device 10 may be enclosed within a distal end of the catheter during passage to the PFO track so as to prevent damage to internal structures of the patient. Once positioned near the PFO track, the abrasion device 10 may be moved distally relative to the end of the catheter by any suitable means known in the art. The abrasion device 10 is then inflated to place the abrasive elements 14 in contact with the tissue defining the PFO track, as shown in FIG. 6. Portions of the SP and SS which define the PFO track are then abraded with the abrasion device 10, for example, by rotating the abrasion device 10 within the PFO track or a linear back and forth motion of device 10 in the PFO track. Abrading the tissue surfaces of the PFO track denudes the endothelium on these tissue surfaces, setting up a healing response in the tissue and tending to cause the PFO track to heal closed over time.

Since the patients are typically heparinized during endovascular procedures, and heparinization may inhibit the adhesion of the tissues to one another, it may be desirable to counter the effect of the heparin with protamine, bringing the patient back to a more normal coagulation state. However, if the heparin is countered, it is desired to have any remaining devices such as the balloon catheter in the inferior vena cava (IVC) to be coated with an appropriate anti-thrombotic coating such as heparin.

In addition to an adverse heparin effect, other problems may prevent adherence between the septum primum (SP) and septum secundum (SS). Various methods are provided herein to enhance or ensure adherence between the abraded tissues. For example, during each heart beat, the RA pressure may be temporarily higher than the LA, potentially preventing the denuded tissue surfaces of the PFO track from adhering to one another long enough to promote long term healing of the surfaces in an apposed and closed condition. Therefore, a more active closure of the PFO track coupled with the abrading step is preferred, at least for a period of several minutes, to assure long-term closure of the PFO track.

Figure 7:
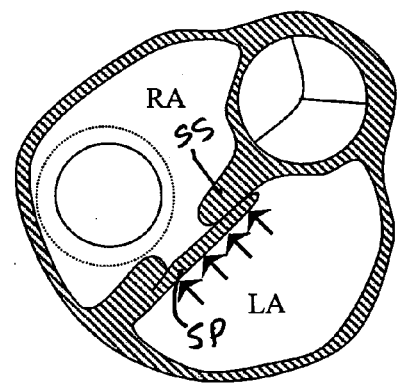
FIG. 7 is a cross-sectional view of the PFO track of FIG. 6, after the abrasion device has been applied, with right atrial pressure reduced to permit closure of the PFO track, according to an aspect of the present invention.

One method of causing a more active temporary closure of the PFO track is illustrated in FIG. 7. After the tissue abrasion step is performed, the abrasion device 10 is removed. Then the venous return to the RA is temporarily reduced. One way to reduce the venous return is to temporarily occlude the inferior vena cava (IVC). This may be performed by positioning an inflatable balloon in the IVC for a period of several minutes to several hours. The reduction of venous return will reduce the pressure in the RA sufficiently such that the LA pressure will be sufficiently greater than the RA pressure, and the greater pressure in the LA will forcibly push the SP against the SS, closing the PFO track. While held against one another, the denuded tissue surfaces of the SS and SP will quickly pass through the initial stages of the healing response and adhere to one another more aggressively than they would under more normal RA pressures.

Figure 8:
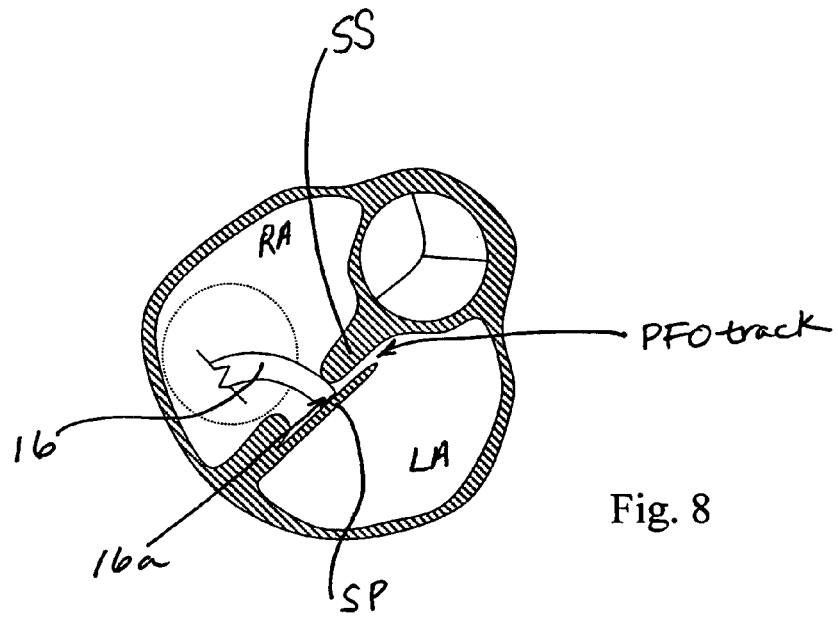
FIGS. 8 and 9 are cross-sectional views of a catheter being used to close a PFO track, according to an aspect of the present invention.
Figure 9:
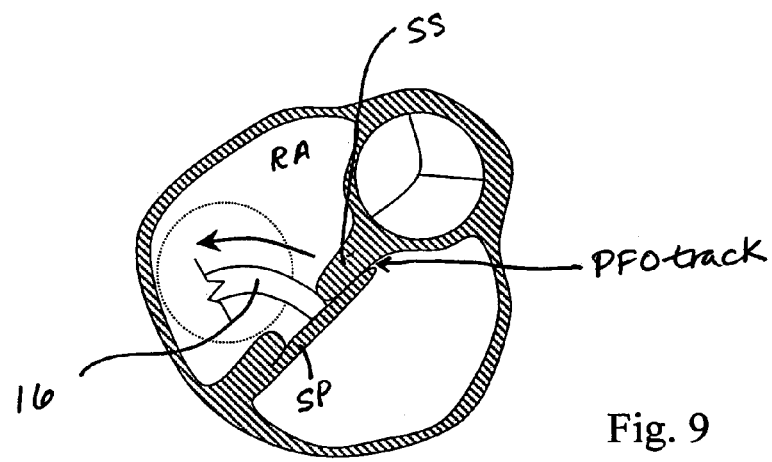

An alternative active temporary closure method is illustrated in FIGS. 8 and 9. In this method, a hollow catheter 16, such as a guiding catheter, is introduced and positioned with its distal end 16a in contact with the septum primum SP, at a location near the PFO track, as shown in FIG. 8. Once in position, a vacuum is created within the lumen of the catheter 16. The vacuum sucks or pulls the tissue of the septum primum SP into the end of the catheter 16, anchoring the catheter 16 to the septum primum SP. The vacuum can be created by any suitable means, such as with the use of a syringe connected in fluid communication with the lumen of the catheter or via aspiration. Once the catheter 16 is anchored to the septum primum SP, the PFO track is temporarily closed by pulling or otherwise manipulating the catheter 16, as shown in FIG. 9, to pull the septum primum SP into apposition with the septum secundum SS.

After a period of several minutes to several hours has passed as one of the above methods is employed, the PFO track will be reliably closed enough to assure the long term healing of the PFO track in a closed condition. At this point, any indwelling devices can be removed from the patient. One advantage of this PFO closure technique is that no foreign body remains in the patient, eliminating issues of foreign body reaction, thrombosis, or fatigue failure.

These techniques of abrading the tissue surfaces of the PFO track and temporarily actively closing the abraded PFO track, as described above in conjunction with FIGS. 6-9, may be individually combined with additional closure devices and methods described below.

According to another aspect of the present invention, a PFO closure device is provided. As embodied herein and shown generically in FIGS. 10 and 11, the PFO closure device comprises a tubular self-flattening closure (SFC) device 50.

The SFC device 50 is configured to be positioned and left inside the PFO track. The SFC device 50 may be fabricated of a sheet or tube, and may comprise polymeric or preferably metallic materials, for example, a preferred material is an alloy of nickel-titanium. Such an alloy can have either shape-memory characteristics or super-elastic characteristics when formed and heat treated at particular temperatures, as is known in the art. Preferably, the SFC device 50 is formed under such conditions to create a device 50 having a parent shape. The device is preferably formed to have a flattened parent configuration, i.e., a configuration which the device will assume when not under other forces, and above its martensite-to-austinite transition temperature. This is accomplished by forming and heat treating the device 50 in a flattened configuration. Then, when the device 50 is deformed to a non-flattened configuration during the delivery steps, it will return to a flattened configuration once the deforming forces are removed.

Figure 10:
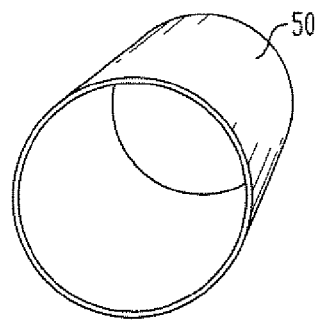
FIG. 10 is a perspective view of an embodiment of a self-flattening closure device in an open configuration according to one aspect of the present invention.
Figure 11:
FIG. 11 is a perspective view of the self-flattening closure device of FIG. 10 in a closed configuration.

The device thus has a first configuration during deployment within the PFO track that is tubular, for example circular, as shown in FIG. 10. The SFC device 50 may be positioned on a balloon catheter, which when inflated, the balloon holds the SFC device 50 in this configuration. When the balloon is deflated, the SFC device 50 returns to a second configuration, the parent shape resembling a flattened tube, as shown in FIG. 11. Within the PFO track, the flattened configuration is oriented such that it tautly maintains a width and a reduced thickness of the PFO track, preventing the PFO track from opening during periods of transient elevated RA pressures. Additionally, the SFC device serves to physically plug any remaining opening of the PFO track as shown in FIGS. 12-14.

Figure 12:
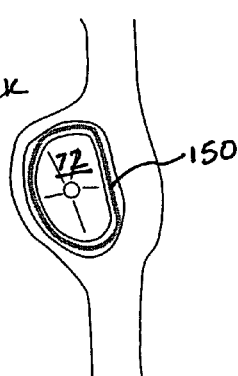
FIGS. 12-14 are cross-sectional views of the self-flattening closure device of FIGS. 10 and 11 with a delivery catheter and being deployed within a PFO track, according to an aspect of the present invention.
Figure 13:
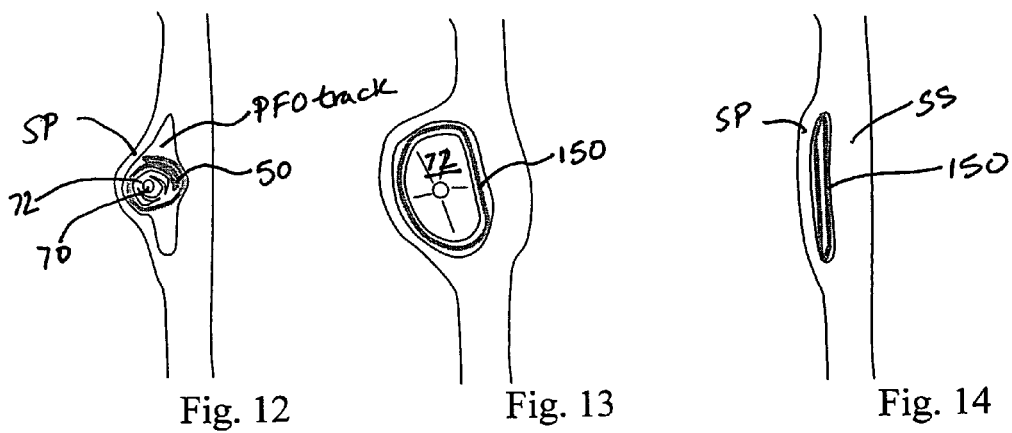
Figure 14:
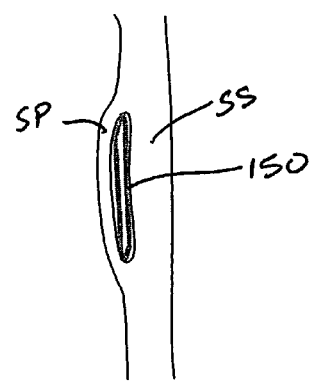

Delivery and deployment of generic SFC device 50 is illustrated in FIGS. 12-14. FIG. 12 shows an end view of the PFO track with the SFC device 50 in a pre-depolyed condition. The SFC device 50 is wrapped around the uninflated balloon 72 of a balloon catheter 70. The balloon catheter 70 with the SFC device 50 is introduced within the venous system, typically at an access site in the femoral vein, and positioned within the PFO track, as shown. The balloon 72 is inflated to allow the SFC device 50 to make contact with the PFO track, as indicated in FIG. 13. When the balloon 72 is deflated and the catheter 70 is removed from the PFO track, the SFC device 50 takes on a flattened configuration, as shown in FIG. 14.

Figure 15:
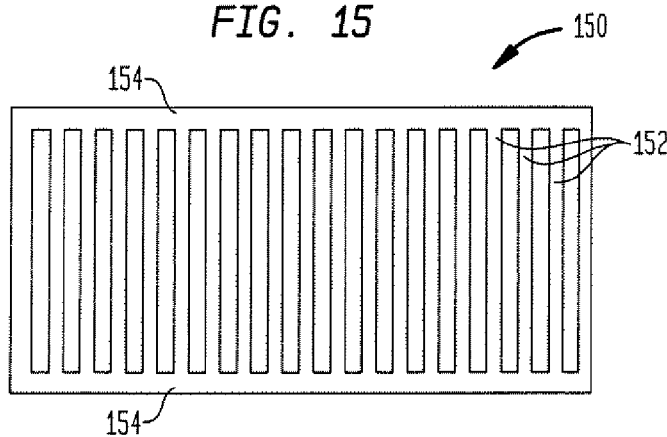
FIG. 15 is a top view of an embodiment of a self-flattening closure device according to one aspect of the present invention.
Figure 16:
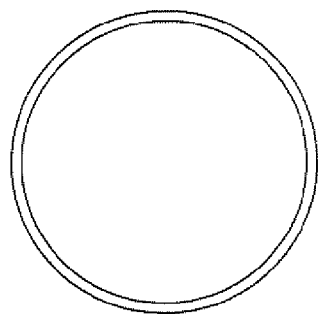
FIG. 16 is an end view of the self-flattening closure device of FIG. 15.
Figure 17:
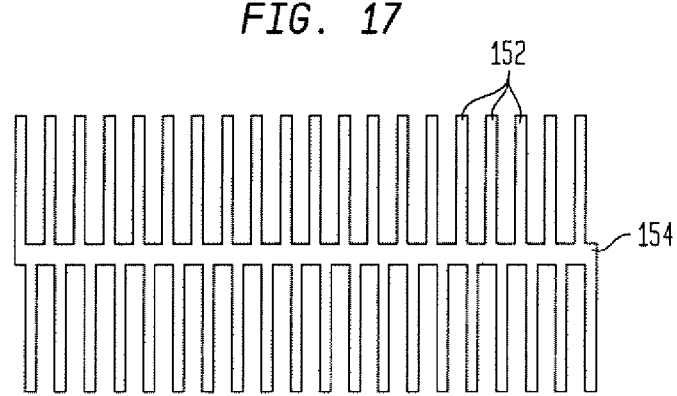
FIG. 17 is a side view of the self-flattening closure device of FIG. 15.

A preferred embodiment of an SFC device 150 is shown in FIGS. 15-20. FIG. 15 is a top view of SFC device 150. FIG. 16 is an end view of SFC device 150, and FIG. 17 is a side view of SFC device 150. SFC device 150 is formed from a metallic tube. Like a vascular stent, portions of the wall of the tube are removed by laser cutting, etching or other process to provide a structure having spaced supports.

Figure 18:
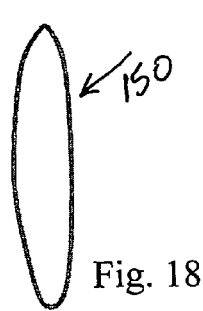
FIG. 18 is an end view of the self-flattening closure device of FIG. 15 in a partially flattened condition.
Figure 19:
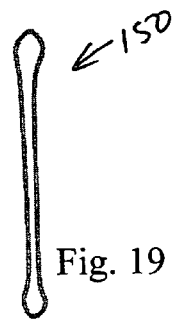
FIG. 19 is an end view of the self-flattening closure device of FIG. 15 in a flattened configuration.
Figure 20:
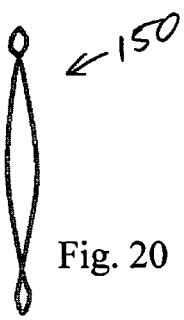
FIG. 20 is an end view of the self-flattening closure device of FIG. 15 in an alternative flattened configuration.

As shown in FIG. 15, the SFC device 150 includes a plurality of circumferential struts 152. The struts 152 comprise slightly less than half the circumference of the top and bottom sides of the SFC device 150. Along SFC device 150, are longitudinal strips 154. Preferably, two strips 54 are formed, spaced 180 degrees from one another, where corners of the device 150 are formed when the device is in the flattened configuration. As shown in FIG. 17, the upper and lower struts 152 may be longitudinally offset from each other. Such a configuration permits the SFC device 150 to be shape-set to a flattened configuration such that the upper and lower struts 152 don't interfere with each other once the device takes on its flattened configuration. That is, when the device 150 collapses from a tubular configuration to a flattened configuration, the struts 152 from a top half of the tube fit between the struts 152 of the bottom half of the tube. The offset further allows the SFC device 150 to be formed in a parent shape such that the struts 152 are actually pushed through or over-set relative to each other (FIG. 20). When such a parent shape is deformed in the SFC device 150 due to other forces, as shown in FIG. 18, the device 150 is urged toward a flattened configuration (FIG. 19) with the struts 152 of the top half of the device being alternately positioned between struts 152 of the bottom half of the device when the other forces are removed. The top and bottom struts 152 can then actually move past each other in the absence of any other forces (FIG. 20), i.e., the top struts 152 pass through the spaces between the bottom struts 152 until the parent configuration is achieved. By forming the SFC device 150 with such an over-set parent shape, the SFC device 150 more aggressively takes on a flattened configuration when positioned within the PFO track, particularly when further tissue attaching mechanisms are employed, as described below.

Figure 21:
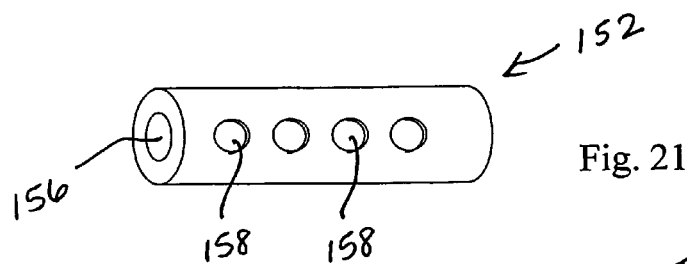
FIG. 21 is an enlarged perspective view of a strut of the self-flattening closure device of FIG. 15.
Figure 22:
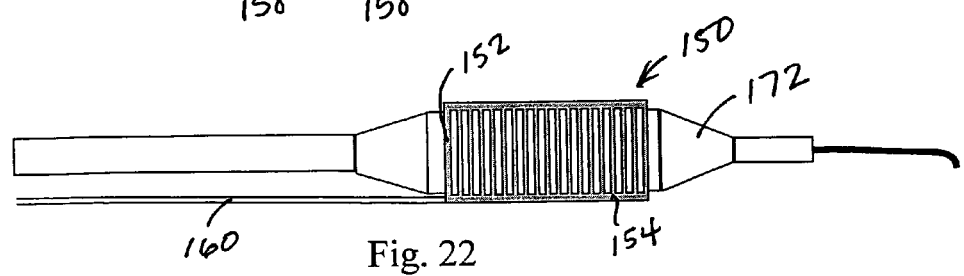
FIG. 22 is a side view of the self-flattening closure device of FIG. 15 on a delivery catheter and connected to an adhesive lumen, according to an aspect of the present invention.

According to another aspect of the invention, the SFC device 150 may include an adhesive tissue attaching mechanism. As embodied herein and shown in FIG. 21, at least some of the struts 152 include a hollow lumen 156 and may be placed in fluid communication with an adhesive delivery lumen 160 (see FIG. 22). The lumens 156 of struts 152 are in fluid communication with a lumen (not shown) which extends within one of the longitudinal struts 154 of the SFC device 150 and is in fluid communication with adhesive delivery lumen 160. Struts 152 may also include a plurality of outwardly directed holes 158, which provide for delivery of an adhesive from the struts 152 to the tissue surfaces defining the PFO track. A preferred adhesive is one that cures upon exposure to moisture, such as a cyanoacrylate. Other suitable adhesives, such as, for example, fibrin glue, a two-part epoxy, or polyurethane, may be used.

In use, the SFC device 150 is positioned on a balloon 172 of a balloon catheter 170. A detachable tube defines an adhesive delivery lumen 160, and provides for adhesive to be delivered to the lumens of struts 152, 154. The delivery lumen 160 is connected to a source of adhesive at a proximal end of the catheter 170, by any suitable means known in the art. The SFC device 150 on the balloon catheter 170, carrying SFC device 150, is passed from an access site, preferably in the femoral vein, into the PFO track (FIG. 23). When the balloon 172 is expanded, as in FIG. 24, a suitable adhesive 162 is injected through lumen 160, through the lumen in longitudinal strut 154, into lumens 156 of hollow struts 152 until it emerges from the holes 158 and contacts the walls of the PFO track. The detachable tube forming lumen 160 is then removed from the SFC device 50 by a suitable detachment mechanism, for example, by a breakaway section that breaks upon torsion. After the adhesive cures, the SFC device 150 is firmly attached to the tissue. Once sufficient curing has taken place to ensure that the SFC device 150 will remain attached to the walls of the PFO track, the balloon 172 is deflated and the catheter 170 is removed, allowing the SFC device 150 to flatten (FIG. 25). Since the parent shape is preferably an over-set flattened shape as described above, the SFC device 150 will aggressively form a flattened shape, bringing the walls of the PFO track, which are adhered to the SFC device 150, in close apposition, and thus closing the PFO track (FIG. 25). Over time, additional scar tissue will form within and around the SFC device 150, creating a long-term robust seal of the PFO track. The healing response following implantation of the various embodiments of the SFC device 150 may be further enhanced by prior abrading of the PFO track, as described above in connection with the device of FIG. 5.

Alternatively, it may be possible to deflate and remove the balloon 172 and catheter 170 prior to curing of the adhesive.

In such a case, the SFC device 150 will flatten prior to the walls of the PFO track adhering to the device 150. Therefore, it would be desirable to use one of the methods described with respect to FIGS. 7-9 to press the walls of the PFO track into the SFC device 150 while the adhesive cures.

According to another aspect of the present invention, an alternative PFO closure device is provided. As embodied herein and shown in FIGS. 26-32, the PFO closure device may comprise a porous balloon catheter. FIG. 26 shows the distal end of a balloon catheter having a porous balloon, herein after referred to as a porous balloon catheter (PBC) 180. PBC 180 includes an inflatable balloon 182 having a plurality of small holes 184 that perforate the balloon 182. FIG. 27 shows a cross-section of the porous balloon 182 in an inflated state and FIG. 28 shows a cross-section of the porous balloon 182 in a deflated state. A detachable tube 186 is connected to a proximal end 188 of the balloon 182.

Use of the PBC 180 in closing a PFO track is illustrated in FIGS. 29-32. The PBC 180 is introduced into the venous circulation through standard techniques, and the balloon 182 is positioned within the PFO track, as shown in FIG. 29. The balloon 182 is then inflated with a fluid that exhibits adhesive-like qualities once cured. Initially, the balloon 182 inflates, expanding the PFO track and making circumferential contact with the tissue defining the PFO track, as shown in FIG. 30. Further pressurization of the balloon 182 then causes some of the liquid adhesive to squeeze out of the pores and form an adhesive film 190 between the walls of the PFO and the outer surface of the balloon 182 (also shown in FIG. 30). Once the adhesive leaves the balloon 182, it cures upon contact with the moist tissue defining the PFO track. As the cure of the adhesive progresses from the walls of the PFO track towards the liquid adhesive inside the balloon 182, the balloon 182 is deflated, bringing the walls of the PFO track, which are now adhered to the balloon 182 via the adhesive film 190, along with it. Once the balloon 182 is deflated, a thin film of adhesive remaining on the inside of the balloon 182 is allowed to cure, and the PFO track is closed (FIG. 31), leaving balloon 182 and adhesive 190 therein. The detachable tube 186 is then removed by a suitable detachment mechanism, such as that described above in connection with the removable tube of the SFC device 150. The bonded-in balloon 182 is left behind in the PFO track (FIG. 32).

The bonded-in balloon 182 will heal in place, resulting in a robust long-term closure of the PFO track. This closure technique results in a minimum amount of foreign body with virtually no contact with blood in either the RA or LA, and as with all devices within the present application, little chance or consequence of mechanical fatigue failure. Also, the PBC 180 and method could be combined with a prior abrading step, as previously described in connection with the device of FIG. 5.

Preferably, the balloon 182 is sized to have a diameter of a size relatively similar to the diameter of the PFO track once expanded, i.e., the perimeter of the balloon is approximately equal to the perimeter of the PFO track, and a length equal to or somewhat shorter than the length of the PFO track. Suitable biocompatible polymers for the porous balloon are preferably polyethylene, expanded polytetrafluoroethylene, PET, Nylon, silicone, polyurethane, or Pebax. The balloon 182 is preferably inflatable by a fluid adhesive. A preferred adhesive is one which cures upon exposure to moisture, such as a cyanoacrylate. The adhesive may be provided to balloon 182 by, for example, a lumen in tube 186 connected to a source of adhesive.

Alternatively, the balloon 182 of the PBC 180 need not be left in the PFO track. In such an embodiment, the tube 186 need not be detachable. In use, the porous balloon 182 is positioned in the PFO track and inflated as shown in FIGS. 29 and 30. However, the balloon 182 is deflated and removed prior to curing of the adhesive such that the balloon surface does not adhere to the wall of the PFO track. Thus, after removal of balloon 182, adhesive covers at least some of the walls of the PFO track. In this embodiment, it is preferred that the adhesive not cure instantly, but rather take at least a few minutes, providing sufficient time to remove the balloon 182 and catheter 180 without causing adhesion between the balloon 182 and the walls of the PFO track. Suitable adhesives for this embodiment are similar to those discussed above, but it is important to select an adhesive with a long enough cure time to minimize curing while the balloon 182 is still present in the PFO track.

In addition, in this embodiment where balloon 182 is not left in the PFO track, the PFO track may be forced closed utilizing any of the steps described above in connection with FIGS. 7-9. Once the adhesive is sufficiently cured, the venous return can be brought back to normal, if the method shown in FIG. 7 is employed, or the catheter with vacuum can be removed if the method employed in FIGS. 8 and 9 is employed, resulting in a robust closure of the PFO track. In this embodiment, only a relatively small amount of a biocompatible adhesive is left behind in the PFO track. And again, for this embodiment, a prior denudation of the walls of the PFO track may further enhance the robustness of the PFO track closure.

According to another aspect of the present invention, an alternative embodiment of a PFO closure device is provided. As embodied herein and shown in FIGS. 33A and 33B, the PFO closure device comprises a balloon catheter 280 having a porous balloon 282. Balloon catheter 280 includes a shaft 286 attached to a proximal end 288 of an inflatable balloon 282. The shaft 286 may or may not be detachable. The balloon 282 comprises two layers, an inner layer 283a, which is not porous, and an outer layer 283b, which is porous. The dual layer balloon 282 is connected to the catheter shaft 286, having a first lumen 286a in fluid communication with the interior of the inner layer 283a, and a second lumen 286b in fluid communication with a space 285 between the inner and outer layers 283a, 283b. The second lumen 286b is used for delivery of an adhesive, while the first lumen 286a is used for inflation and deflation of the dual layer balloon 282. Since the inner layer 283a is non-porous, inflation and deflation of this dual layer balloon 282 can be performed completely independently of adhesive delivery.

In use, balloon 282 is used in a manner similar to that described above with respect to FIGS. 26-30. The balloon 282 is introduced to the PFO track, then inflated, and adhesive is delivered via the porous outer layer 283b to the walls of the PFO track. The balloon 282 is then deflated and removed, optionally followed by forced closure of the PFO track, as previously described in connection with FIGS. 7-9. Alternatively, the balloon 282 might be detached from the catheter shaft and left implanted in the PFO track as previously described with respect to FIGS. 26-32.

Figure 33A:
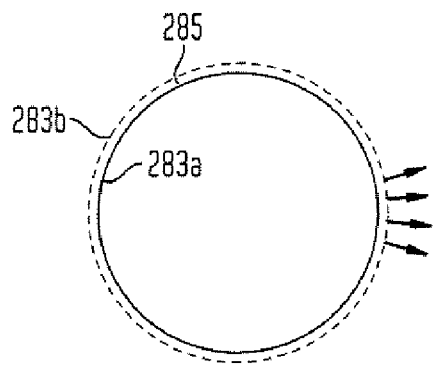
FIG. 33A is a cross-sectional view of an alternative embodiment of a porous balloon in an inflated condition according to another aspect of the invention.
Figure 33B:
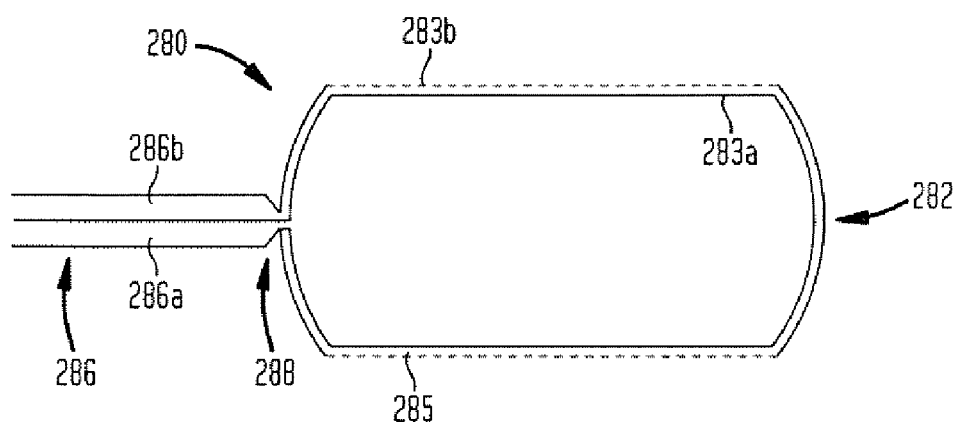
FIG. 33B is a longitudinal cross-sectional view of the porous balloon of FIG. 33A connected to a catheter.
Figure 34:
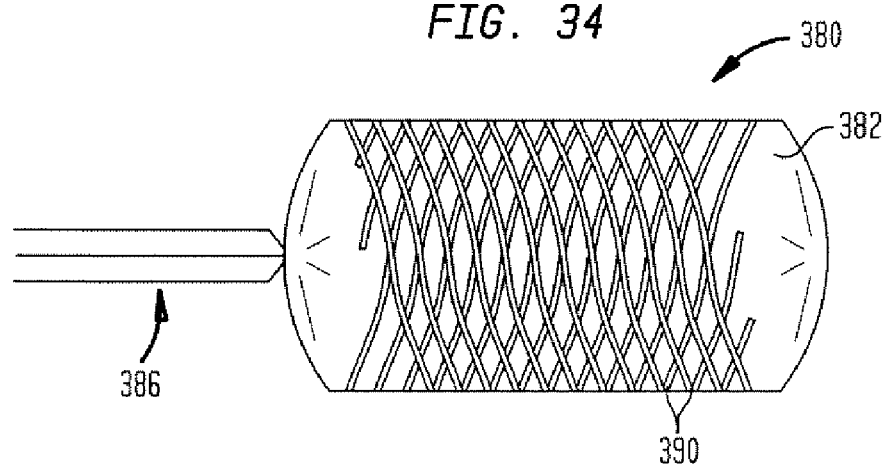
FIG. 34 is a side view of a porous balloon catheter according to one aspect of the present invention.

According to another aspect of the present invention, a PFO closure device is provided. As embodied herein and shown in FIGS. 34-38, a dual layer porous balloon, similar to the balloon shown in FIGS. 33A and 33B, is provided. In this embodiment, the balloon 382 is connected to a detachable shaft 386. The interior surface 381 of the balloon 382 also includes an adherence mechanism 390. Adherence mechanism 390 preferably includes strips of a mechanical interlocking structure, such as Velcro. Strips of Velcro are preferably arranged in a helical fashion on the interior surface 381 of the balloon 382. The strips are positioned such that rows of "hooks" H alternate with rows of "loops" L. The adherence mechanism 390 serves to maintain the balloon 382 in a deflated condition upon removal of inflation medium from the balloon 382.

Figure 35:
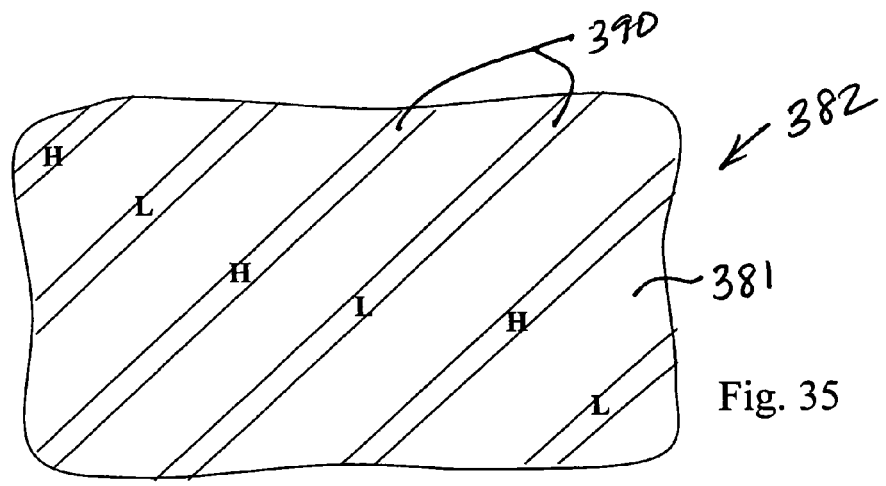
FIG. 35 is a first longitudinal cross-sectional view of the balloon of FIG. 34.
Figure 36:
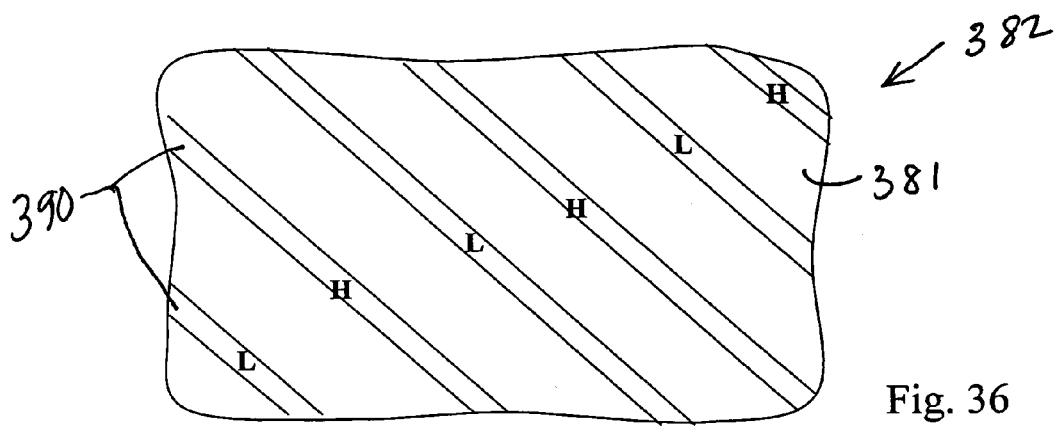
FIG. 36 is a second longitudinal cross-sectional view of the balloon of FIG. 34 taken from an opposite side than FIG. 35.
Figure 38:
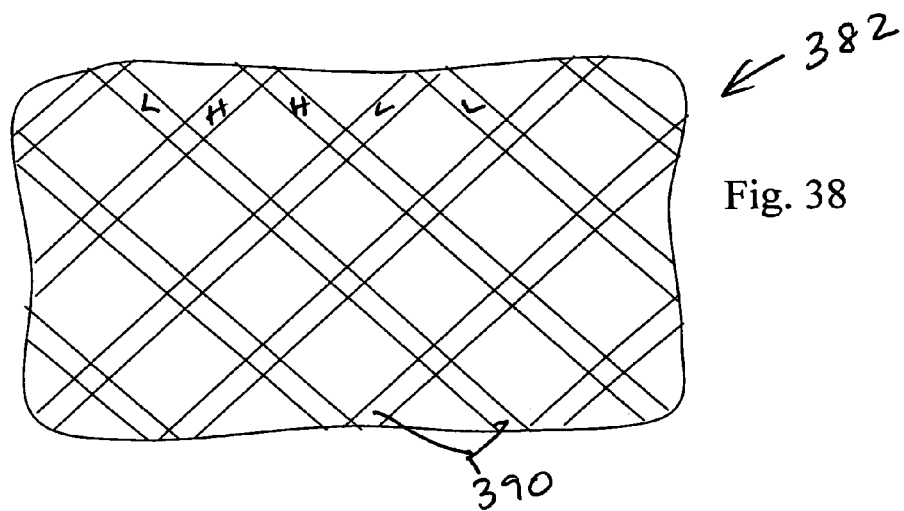
FIG. 38 is a cross-sectional top view of the porous balloon of FIG. 34 in the deflated condition and taken along line A-A of FIG. 37.
Figure 37:
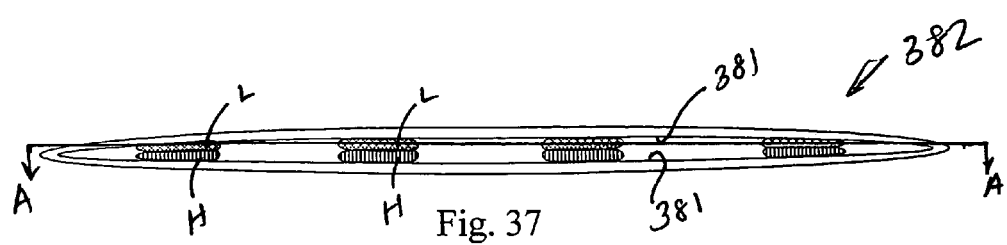
FIG. 37 is a cross-sectional view of the porous balloon of FIG. 34 in a deflated condition.

FIG. 35 shows the alternating strips of hooks (H) and loops (L) on the inner surface 381 of one half of the balloon 382, and FIG. 36 shows the alternating strips on the inner surface 381 of the opposite half of the balloon 382. When the balloon 382 is deflated, the inner surfaces 381 of the two balloon halves come together, forcing the Velcro strips to make contact in at least a plurality of locations where they intersect (FIGS. 37-38).

In use, the porous balloon catheter is used in a similar manner as that described in connection with the steps shown in FIGS. 26-33B. The balloon 382 is introduced to the PFO track, inflated at a sufficiently high pressure to disengage the Velcro strips of the adherence mechanism, and adhesive is delivered via the porous outer layer 383b to the walls of the PFO track. The balloon 382 is then deflated and the rows of Velcro on the interior 381 of the balloon 382 come into contact with one another, holding the balloon 382 in a flattened configuration. The catheter shaft 386 is detached from the balloon 382, and the balloon is left implanted in the PFO track as previously described with respect to FIGS. 26-32.

According to another aspect of the invention, an alternative embodiment of a PFO closure device is provided. As embodied herein and shown in FIGS. 39-42, the PFO closure device includes a delivery device 400 carrying suture-anchor assemblies 401. Each suture-anchor assembly 401 includes a barbed anchor 402 connected to a suture tie 404. Suitable suture tie materials include those typically used in surgical closure of PFO tracks, such as degradable or non-degradable type commercially available suture material, monofilament or braided type commercially available suture material. The barbed anchors 402 and suture ties 404 are used to mechanically close the PFO track from within the lumen of the PFO track.

Figure 39:
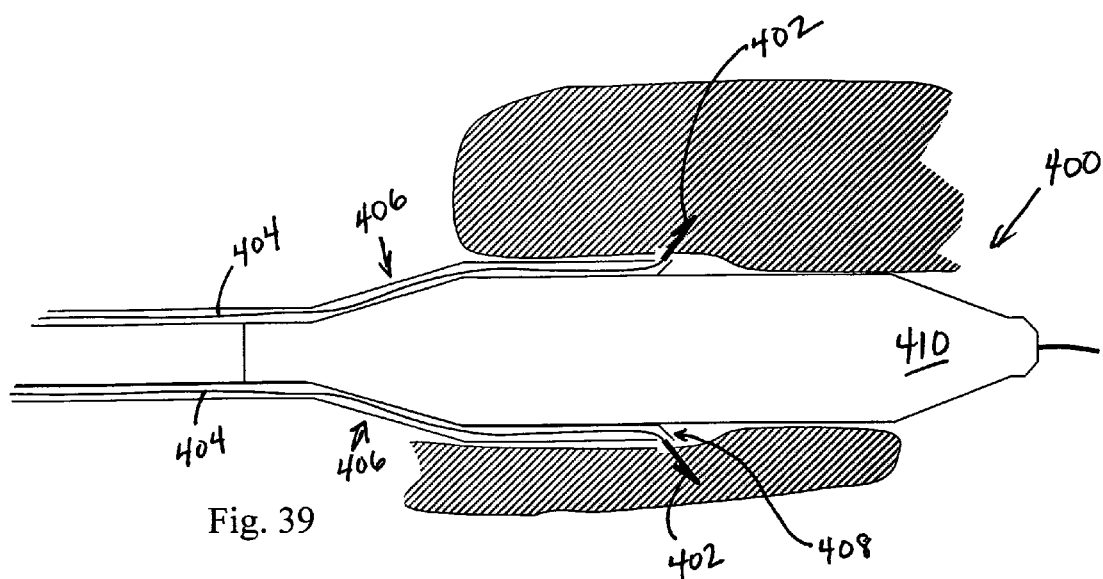
FIG. 39 is a cross-sectional view of a PFO closure device according to another aspect of the present invention.

The delivery device 400 contains a plurality of suture lumens 406, one for each suture-anchor assembly 401. Each suture lumen 406 terminates in an opening 408. As shown in FIG. 39, each suture lumen 406 is located on an opposite side of the delivery device 400, such that the suture lumens are spaced approximately 180 degrees apart from one another. An expandable head of the delivery device, for example a balloon 410, allows the suture lumen openings 408 to be displaced radially outward. This causes the PFO track to be dilated and stretched taut, which facilitates penetration of the anchors into the tissue surrounding the PFO track.

Figure 40:
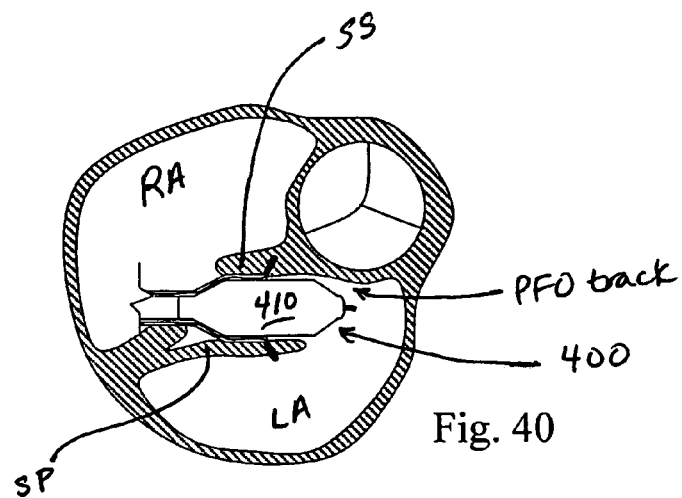
FIGS. 40-42 are cross-sectional views of the PFO closure device of FIG. 39 in use to close a PFO track, according to an aspect of the present invention.

In use, the delivery device 400 is positioned within the PFO track, in a non-deployed condition. The suture-anchor assemblies 401 are positioned within the suture lumens 406, with the anchors 402 also residing in the suture lumens 406. Once the suture lumen openings 408 are in a desired position within the PFO track, the expandable head 410 is deployed (i.e., the balloon 410 is inflated). Then the suture-anchor assemblies 401 are advanced until the anchors 402 emerge from the suture lumen openings 408 and penetrate into the tissue forming the PFO track. To assist in supporting suture anchor assemblies 401 during advancement and penetration, it may be useful to surround the suture ties 404 with a separate tubular support members (not shown), which are advanced with the suture anchor assemblies 401. Tubular support members are removed proximally after anchors 402 are deployed. This step in the procedure is illustrated in FIGS. 39 and 40.

Figure 41:
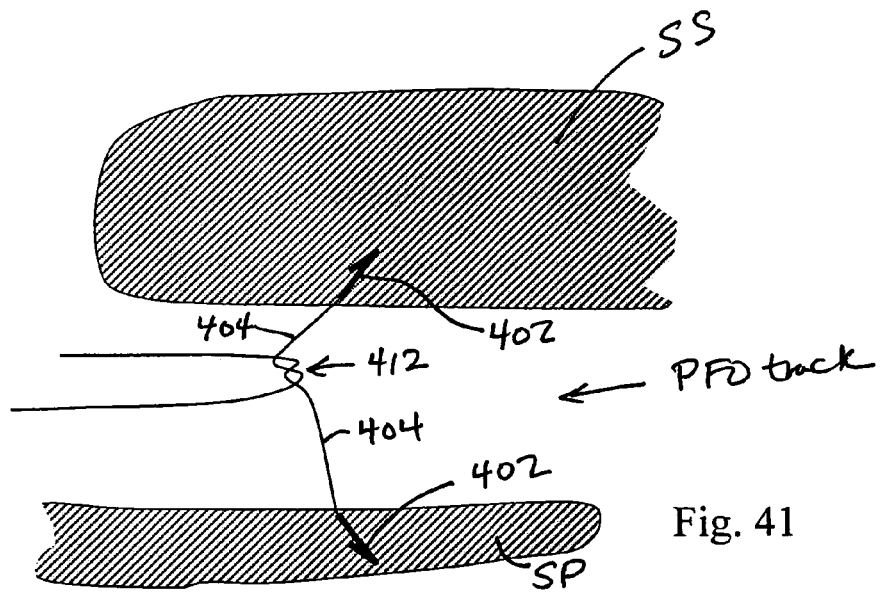
Figure 42:
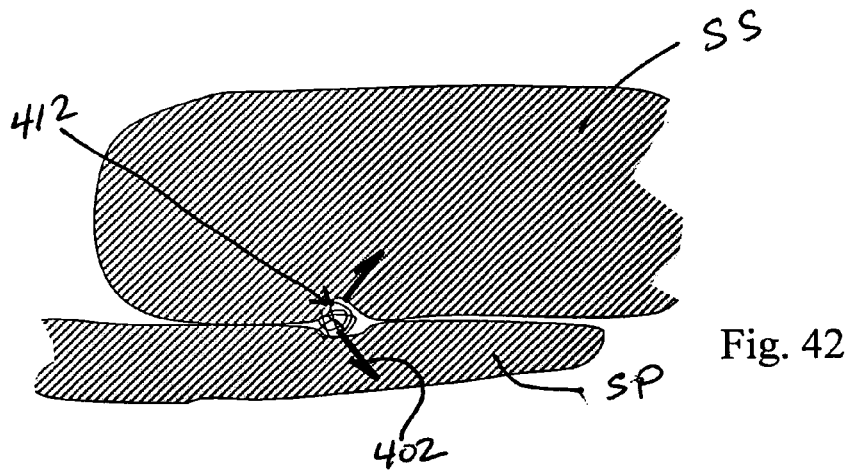

Once the anchors are firmly engaged in the tissue, balloon 410 is deflated and the delivery device 400 is removed, leaving the sutures 404 extending outside the access site of the patient. While two sutures are shown, it is contemplated that any number of sutures, two or more, could be placed. The sutures 404 are tied into a knot 412 by any suitable method, as shown in FIG. 41, and the knot 412 is pushed towards the anchors 402 with the help of a knot pushing device (not shown). Once the knot 412 is tightened against the walls of the PFO track, the walls are brought into apposition, and the suture tails are cut, resulting in the configuration illustrated in FIG. 42. Cutting of the suture tails can be accomplished by any suitable endovascular cutting mechanism known in the art.

While these suture and anchor assemblies 401 can be used as a sole mechanism for PFO closure, it is preferable to combine this device with a prior abrading of the walls of the PFO track as described previously. When combined as such, the PFO track will heal to a robustly closed condition.

Figure 43:
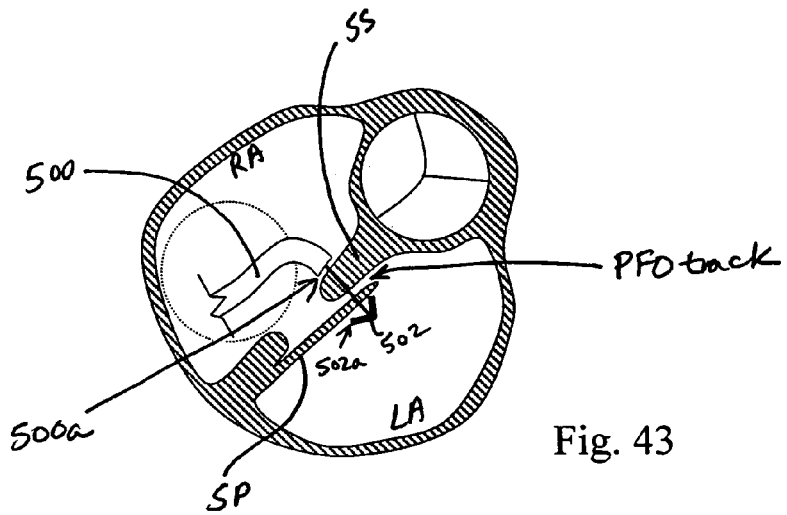
FIG. 43 is a cross-sectional view of an alternative PFO closure device disposed within the right atrium, according to an aspect of the present invention.
Figure 44:
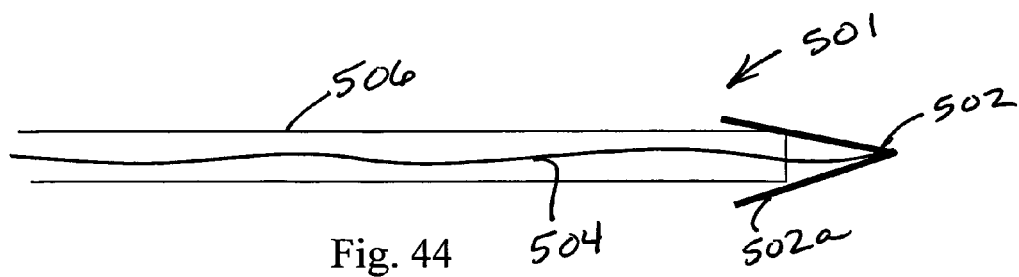
FIG. 44 is a cross-sectional view of an anchor and suture used with the PFO device of FIG. 43, according to an aspect of the present invention.
Figure 45:
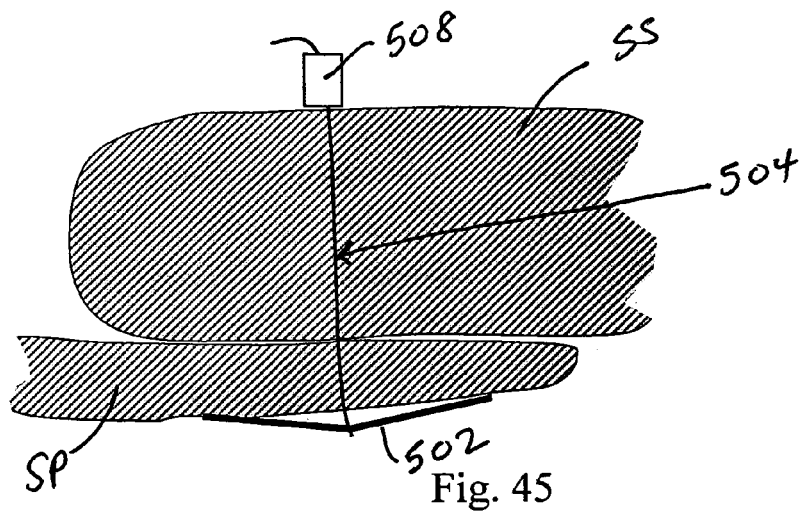
FIG. 45 is a cross-sectional view of the anchor and suture of FIG. 44 after they have been deployed to close the PFO track, according to an aspect of the present invention.

According to another aspect of the invention, another embodiment of a PFO closure device is provided. As embodied herein and shown in FIGS. 43-45, a delivery catheter 500 is positioned within the RA such that the tip 500a is adjacent the SS, near the PFO track. A suture and anchor assembly 501 comprising a suture 504 with a barb-like anchor 502 is advanced through the SS, and through the SP, bridging the PFO track roughly perpendicular to the longitudinal aspect of the PFO track (FIG. 43). Suitable suture tie materials include those typically used in surgical closure of PFO tracks, such as degradable or non-degradable type commercially available suture material, monofilament or braided type commercially available suture material. Barb-like anchor 502 preferably includes tines 502a which are self-expanding once they emerge from the tissue. Once the barb-like anchor 502 is passed through the SP, the barb opens up and acts as a strong securement for the suture. Although only one suture and anchor assembly 501 is illustrated in FIGS. 43-45, more than one may be used as necessary to ensure sufficient closure of the PFO track.

To help facilitate advancement of the suture and anchor assembly 501 across the SS and SP, it may be necessary to provide additional support to the relatively flexible suture 504. FIG. 44 shows a support tube 506 surrounding the suture. Support tube 506 preferably has high column support, but enough lateral flexibility to negotiate any curves within the delivery catheter 500. Suitable materials include metals and relatively rigid polymers. Preferred metals include Ni—Ti alloy and stainless steel. Preferred polymers include polyimide and PEEK. The support tube 506 helps advance the anchor 502 and suture 504 across the tissue, and is removed after the anchor is deployed across the SP.

After the barb-like anchor 502 is deployed, a lock device 508, preferably a one-way device, such as, for example, a releasable fixation mechanism (disclosed in U.S. patent application Ser. No. 09/870,813, filed on Jun. 1, 2001, and entitled "Closure Devices, Related Delivery Methods and Tools, and Related Methods of Use," the entire disclosure of which is incorporated herein by reference), is advanced along the suture 504, pulling the SP and SS together. The remaining suture length is then cut by suitable techniques. While this suture-based concept may be performed as a sole therapy it is preferable to combine this suture closure with a prior abrading of the tissue forming the PFO track to facilitate a robust long-term closure of the PFO.

Other embodiments of the invention will be apparent to those skilled in the art from consideration of the specification and practice of the invention disclosed herein. The specification and examples are exemplary, with a true scope and spirit of the invention being indicated by the following claims.

What is claimed is:

1. A method of treating a patent foramen ovale in a heart, the method comprising:

advancing a catheter device having a proximal end and a distal end through vasculature of a patient to position the distal end adjacent the patent foramen ovale;

delivering a self-closing closure device from the catheter to contact tissues adjacent the patent foramen ovale, wherein the delivered self-closing closure device closes to bring together the tissues of the patent foramen ovale, and wherein delivering the self-closing closure device comprises driving multiple tissue attachment members coupled with a self-closing stent into the tissues; and wherein the self-closing stent comprises a generally tubular member that collapses upon itself.

2. The method of claim 1, wherein the closure device is biodegradable.

3. The method of claim 1, further comprising extending a portion of the at least one closure device within the patent foramen ovale to apply lateral force to tissue at opposite sides of the patent foramen ovale, thus bringing together tissue between the opposite sides.

4. The method of claim 1, further comprising passing the catheter body over a guidewire.

5. The method of claim 1, further comprising visualizing at least one of the patent foramen ovale and tissue surrounding the patent foramen ovale with at least one visualization device coupled with the catheter body near the distal end.

* * * * *